United States Patent
Taki et al.

(10) Patent No.: US 9,637,722 B2
(45) Date of Patent: May 2, 2017

(54) PRODUCTION METHOD OF POLYURETHANE POROUS MEMBRANE TO BE USED FOR AT LEAST ONE OF APPLICATIONS OF CELL CULTURE AND CANCER CELL GROWTH INHIBITION

(71) Applicants: TOYODA GOSEI CO., LTD., Kiyosu-shi, Aichi-ken (JP); National University Corporation Yamagata University, Yamagata-shi, Yamagata (JP)

(72) Inventors: Seitaro Taki, Kiyosu (JP); Hisashi Mizuno, Kiyosu (JP); Hiroyuki Nakagawa, Kiyosu (JP); Toshiyuki Hagiyama, Kiyosu (JP); Atsuki Yoshimura, Kiyosu (JP); Masaru Tanaka, Yonezawa (JP); Ayano Sasaki, Yonezawa (JP); Toshifumi Takahashi, Yamagata (JP); Tsuyoshi Ohta, Yamagata (JP)

(73) Assignees: TOYODA GOSEI CO., LTD., Aichi-pref. (JP); National University Corporation Yamagata University, Yamagata (JP)

( * ) Notice: Subject to any disclaimer, the term of this patent is extended or adjusted under 35 U.S.C. 154(b) by 206 days.

(21) Appl. No.: 14/320,914

(22) Filed: Jul. 1, 2014

(65) Prior Publication Data

US 2015/0017725 A1    Jan. 15, 2015

(30) Foreign Application Priority Data

Jul. 9, 2013 (JP) .................................. 2013-143371
May 20, 2014 (JP) .................................. 2014-104225

(51) Int. Cl.
| | | |
|---|---|---|
| C08J 9/08 | (2006.01) | |
| C12N 5/00 | (2006.01) | |
| B01D 67/00 | (2006.01) | |
| B01D 71/54 | (2006.01) | |
| C08J 9/12 | (2006.01) | |
| B05D 3/10 | (2006.01) | |
| B05D 5/00 | (2006.01) | |

(52) U.S. Cl.
CPC ....... C12N 5/0068 (2013.01); B01D 67/0023 (2013.01); B01D 71/54 (2013.01); B05D 3/108 (2013.01); B05D 5/00 (2013.01); C08J 9/08 (2013.01); C08J 9/125 (2013.01); B01D 2325/08 (2013.01); C08J 2201/032 (2013.01); C08J 2203/02 (2013.01); C08J 2203/10 (2013.01); C08J 2207/10 (2013.01); C08J 2375/04 (2013.01); C12N 2533/30 (2013.01)

(58) Field of Classification Search
CPC .. C12N 5/0068; C12N 2533/30; B05D 3/108; B05D 5/00; B05D 67/0023; B05D 71/54; B05D 2325/08; C08J 9/08; C08J 9/125; C08J 2203/02; C08J 2203/10; C08J 2207/10; C08J 2201/032; C08J 2375/04

See application file for complete search history.

(56) References Cited

U.S. PATENT DOCUMENTS

| | | | | |
|---|---|---|---|---|
| 3,595,732 | A * | 7/1971 | Tingerthal | ............... C08J 9/28 264/41 |
| 4,137,200 | A * | 1/1979 | Wood | ................... A61K 6/09 521/159 |
| 4,365,025 | A * | 12/1982 | Murch | ............. C08G 18/4833 521/159 |
| 4,439,391 | A * | 3/1984 | Hung | ............... A61F 13/00991 264/293 |
| 5,650,450 | A * | 7/1997 | Lovette | ............ C08G 18/4833 521/112 |
| 2003/0203182 | A1 | 10/2003 | Thomson | |
| 2007/0275156 | A1 | 11/2007 | Tanaka et al. | |
| 2009/0246865 | A1 | 10/2009 | Yamazaki et al. | |

FOREIGN PATENT DOCUMENTS

| | | |
|---|---|---|
| EP | 1 626 109 A1 | 2/2006 |
| GB | 1 227 124 | 4/1971 |
| JP | 2002-347107 A | 12/2002 |
| JP | 2005-152526 A | 6/2005 |
| JP | 2007-089737 A | 4/2007 |
| JP | 2009-242495 A | 10/2009 |
| WO | 2005/074627 A2 | 8/2005 |
| WO | 2006/118248 A1 | 11/2006 |
| WO | 2008/001865 A1 | 1/2008 |

* cited by examiner

*Primary Examiner* — John Cooney
(74) *Attorney, Agent, or Firm* — Posz Law Group, PLC

(57) ABSTRACT

A polyurethane porous membrane is produced by a simple method to be used for at least one of applications of cell culture and cancer cell growth inhibition. The production method of the polyurethane porous membrane to be used for at least one of the applications of cell culture and cancer cell growth inhibition comprises: a first step of forming a layer of a polyurethane material which is uncured, on a substrate; and a second step of supplying water vapor to an exposed surface of the layer of the polyurethane material formed on the substrate, which is away from the substrate, so as to cure the polyurethane material and provide the layer of the polyurethane material with a porous structure having a plurality of irregularities on the exposed surface.

12 Claims, 28 Drawing Sheets

Fig.8

|  |  | Sample 1 | Sample 2 |
|---|---|---|---|
| Polyol | Polyether | 100 parts by mass (5.003g) | 100 parts by mass (5.003g) |
|  | Polymer polyol | 0 | 0 |
| Crosslinking agent | Diethylene glycol | 18 parts by mass (0.904g) | 18 parts by mass (0.904g) |
| Modifier | Water | 7 parts by mass (350 μL: ,0.358g) | 7 parts bymass (350 μL: ,0.358g) |
| Isocyanate | Polyol-modified MDI | 82.5 parts by mass (4.141g) | 82.5 parts by mass (4.141g) |
| Diluting solvent | Tetrahydrofuran | 178 parts by mass (10mL) | 178 parts by mass (10mL) |
| Curing condition (atmosphere) | | at 40°C overnight (Water vapor) | at 60°C overnight (Dry) |

Fig.9

| | Sample 1 | Sample 2 |
|---|---|---|
| Curing condition | at 40°C overnight | at 60°C overnight |
| Atmosphere | Water vapor | Dry |
| Top surface at 3000-fold | 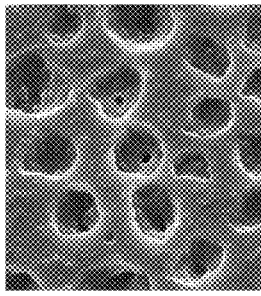 | 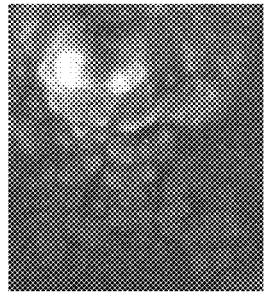 |
| Bottom surface at 3000-fold | 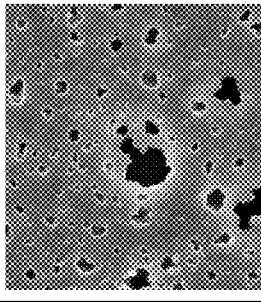 | — |
| Cross section at 1000-fold | 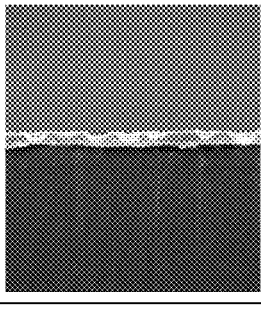 | 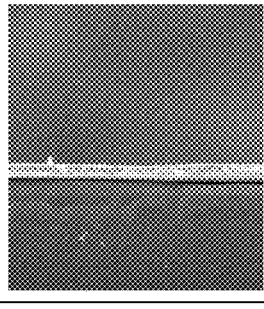 |
| Membrane thickness at the crest ($\mu$m) | 5.8 ±0.5 | 3.8 ±0.3 |
| Membrane thickness at the trough ($\mu$m) | 3.2 ±0.6 | — |
| Presence of through holes | Present | None |
| Size of top surface pore ($\mu$m) | 7 ±2 | None |
| Size of maximum bottom surface pore ($\mu$m) | 7 | None |
| Through hole | Through holes of less than 10 $\mu$m were present | None |

Fig.10

|  |  | Sample 3 | Sample 4 | Sample 5 | Sample 6 | Sample 7 | Sample 8 |
|---|---|---|---|---|---|---|---|
| Polyol | Polyether | 100 parts by mass (5.010g) | 100 parts by mass (5.010g) | 100 parts by mass (5.010g) | 0 | 0 | 0 |
|  | Polymer polyol | 0 | 0 | 0 | 100 parts by mass (5.02926g) | 100 parts by mass (5.02926g) | 100 parts by mass (5.02926g) |
| Crosslinking agent | Diethylene glycol | 18 parts by mass (0.910g) | 18 parts by mass (0.910g) | 18 parts by mass (0.910g) | 0 | 0 | 0 |
| Modifier | Water | 7 parts by mass (350 μL: 0.356g) | 7 parts by mass (350 μL: 0.356g) | 7 parts by mass (350 μL: 0.356g) | 7 parts by mass (350 μL: 0.359g) | 7 parts by mass (350 μL: 0.359g) | 7 parts by mass (350 μL: 0.359g) |
| Isocyanate | Polyol-modified MDI | 82.5 parts by mass (4.149g) | 82.5 parts by mass (4.149g) | 82.5 parts by mass (4.149g) | 32.5 parts by mass (1.675g) | 32.5 parts by mass (1.675g) | 32.5 parts by mass (1.675g) |
| Diluting solvent | Tetrahydrofuran | 89 parts by mass (5mL) | 89 parts by mass (5mL) | 89 parts by mass (5mL) | 89 parts by mass (5mL) | 89 parts by mass (5mL) | 89 parts by mass (5mL) |
| Curing condition (atmosphere) |  | at room temperature overnight (Water vapor) | at 60°C overnight (Water vapor) | at 80°C overnight (Water vapor) | at room temperature overnight (Water vapor) | at 60°C overnight (Water vapor) | at 80°C overnight (Water vapor) |

Fig.11

| Curing condition | Sample 3 at room temperature overnight | Sample 4 at 60°C overnight | Sample 5 at 80°C overnight | Sample 6 at room temperature overnight | Sample 7 at 60°C overnight | Sample 8 at 80°C overnight |
|---|---|---|---|---|---|---|
| Atmosphere | Water vapor | Water vapor | Water vapor | Water vapor | Water vapor | Water vapor |
| Top surface at 1000-fold | | | | | | |
| Top surface at 5000-fold | | | | | | |
| Membrane thickness at the crest (μm) | 9.7 ±0.7 | 13.8 ±1.9 | 11.7 ±2.1 | 8.2 ±1.2 | 10.7 ±1.3 | 14.3 ±2.0 |

Fig.12

| | | Sample 9 | Sample 10 | Sample 11 |
|---|---|---|---|---|
| Polyol | Polyether | 100 parts by mass (5.007g) | 100 parts by mass (5.007g) | 100 parts by mass (5.007g) |
| | Polymer polyol | 0 | 0 | 0 |
| Crosslinkingagent | Diethylene glycol | 18 parts by mass (0.902g) | 18 parts by mass (0.902g) | 18 parts by mass (0.902g) |
| Modifier | Water | 7 parts by mass (350 μL:,0.358g) | 7 parts by mass (350 μL:,0.358g) | 7 parts by mass (350 μL:,0.358g) |
| Isocyanate | Polyol-modified MDI | 82.5 parts by mass (4.125g) | 82.5 parts by mass (4.125g) | 82.5 parts by mass (4.125g) |
| Diluting solvent | Tetrahydrofuran | 222.5 parts by mass (12.5mL) | 222.5 parts by mass (12.5mL) | 222.5 parts by mass (12.5mL) |
| Curing condition (atmosphere) | | at 50°C overnight (Water vapor) | at 60°C overnight (Water vapor) | at 60°C overnight (Dry) |

Fig. 13B

|  |  | Sample 9 | Sample 10 | Sample 11 |
|---|---|---|---|---|
| Membrane thickness at the crest ($\mu$m) | | 7.1 ±0.3 | 9 ±1 | 3.9 ±0.3 |
| Membrane thickness at the trough ($\mu$m) | | 1 ±1 | 0.7 ±0.8 | — |
| Presence of through holes | | Present | Present | — |
| Size of top surface pore | SEM magnification at analysis | 1000 | 1000 | — |
| | Average ($\mu$m) | 7.7 | 10.2 | — |
| | Standard deviation | 3.7 | 6.1 | — |
| | Maximum value | 27.2 | 30.4 | — |
| | Minimum value | 0.7 | 1.0 | — |
| Size of bottom surface pore | SEM magnification at analysis | 200 | 200 | — |
| | Average ($\mu$m) | 7.8 | 7.3 | — |
| | Standard deviation | 1.7 | 4.0 | — |
| | Maximum value | 13.7 | 33.8 | — |
| | Minimum value | 1.6 | 1.1 | — |

Fig.14

|  |  | Sample 12 | Sample 13 | Sample 14 |
|---|---|---|---|---|
| Polyol | Polyether | 100 parts by mass (5.004g) | 100 parts by mass (5.004g) | 100 parts by mass (5.004g) |
|  | Polymer polyol | 0 | 0 | 0 |
| Crosslinking agent | Diethylene glycol | 18 parts by mass (0.912g) | 18 parts by mass (0.912g) | 18 parts by mass (0.912g) |
| Modifier | Water | 7 parts by mass (350 μL:,0.358g) | 7 parts by mass (350 μL:,0.358g) | 7 parts by mass (350 μL:,0.358g) |
| Isocyanate | Polyol-modified MDI | 82.5 parts by mass (4.125g) | 82.5 parts by mass (4.125g) | 82.5 parts by mass (4.125g) |
| Diluting solvent | Tetrahydrofuran | 267 parts by mass (15mL) | 267 parts by mass (15mL) | 267 parts by mass (15mL) |
| Curing conditions (atmosphere) | Formation of pores | at 40°C for 30 minutes (Water vapor) | at 50°C for 30 minutes (Water vapor) | at 60°C overnight (Dry) |
|  | Acceleration of curing | at 60°C overnight (Dry) | at 60°C overnight (Dry) |  |

Fig. 15A

| | Sample 12 | | Sample 13 | | Sample 14 |
|---|---|---|---|---|---|
| Curing Condition | at 40°C for 30 minutes | at 60°C overnight | at 50°C for 30 minutes | at 60°C overnight | at 60°C overnight |
| Atmosphere | Water vapor | Dry | Water vapor | Dry | Dry |
| Top surface at 500-fold | | | | | |
| Bottom surface | at 200-fold | | at 500-fold | | — |
| Cross section at 1000-fold | | | | | |

Fig. 15B

|  |  | Sample 12 | Sample 13 | Sample 14 |
|---|---|---|---|---|
| Membrane thickness at the crest ($\mu$m) | | 5.6 ±0.5 | 6.5 ±0.4 | 4.3 ±0.4 |
| Membrane thickness at the trough ($\mu$m) | | 2 ±1 | 0.6 ±0.9 | — |
| Presence of through holes | | Present | Present | — |
| Size of top surface pore | SEM magnification at analysis | 500 | 500 | — |
| | Average ($\mu$m) | 8.7 | 11.1 | — |
| | Standard deviation | 1.5 | 8.7 | — |
| | Maximum value | 14.8 | 56.7 | — |
| | Minimum value | 2.2 | 0.8 | — |
| Size of bottom surface pore | SEM magnification at analysis | 200 | 200 | — |
| | Average ($\mu$m) | 9.3 | 9.9 | — |
| | Standard deviation | 2.3 | 3.6 | — |
| | Maximum value | 22.5 | 36.3 | — |
| | Minimum value | 3.5 | 2.0 | — |

Fig. 16A

| | | Characteristic value | Sample 15 | Sample 16 | Sample 17 | Sample 18 |
|---|---|---|---|---|---|---|
| Polyol | Polyether polyol | Hydroxyl value 37 | — | — | — | — |
| | Polyether polyol | Hydroxyl value 397 | 100 | — | — | — |
| | Polymer polyol | Hydroxyl value 27 | — | — | — | — |
| | Polyester polyol (ethylene adipate-based) | Hydroxyl value 56 | — | 100 | 100 | — |
| | Polycarbonate polyol | Hydroxyl value 55 | — | — | — | 100 |
| Crosslinking agent | Diethylene glycol | — | 18 | 18 | 18 | 18 |
| | Ethylene glycol | — | — | — | — | — |
| Isocyanate | Polyol-modified MDI | NCO% 28.0 | 180.4 | 81.5 | 89.1 | 89.0 |
| | Monomeric MDI | NCO% 33.6 | — | — | — | — |
| | Polyol-modified MDI | NCO% 23.1 | — | — | — | — |
| | Polymeric MDI | NCO% 30.7 | — | — | — | — |
| | Carbodiimide-modified MDI | NCO% 28.7 | — | — | — | — |
| Modifier | Water | — | 7 | 7 | 7 | 7 |
| Diluting solvent | Tetrahydrofuran | — | 267 | 267 | 267 | 267 |
| Type of substrate | | | PP | PP | PP | PP |
| Spin coating condition | | | 5000 rpm for 1 minute | 5000 rpm for 1 minute | 5000 rpm for 1 minute | 5000 rpm for 1 minute |
| Curing conditions (atmosphere) | Formation of pores | | at 40°C for 30 minutes (Water vapor) | at 40°C for 30 minutes (Water vapor) | at 40°C for 30 minutes (Water vapor) | at 40°C for 30 minutes (Water vapor) |
| | Acceleration of curing | | at 60°C overnight (Dry) | at 60°C overnight (Dry) | at 60°C overnight (Dry) | at 60°C overnight (Dry) |
| Membrane thickness at the crest (μm) | | | 5 | 8 | 8 | 7 |
| Average size of top surface pore (μm) | | | 7.2 | 5.9 | 5.1 | 3.4 |

Fig. 16B

| | | Characteristic value | Sample 19 | Sample 20 | Sample 21 | Sample 22 | Sample 23 |
|---|---|---|---|---|---|---|---|
| Polyol | Polyether polyol | Hydroxyl value 37 | 100 | 100 | 100 | 100 | 100 |
| | Polyether polyol | Hydroxyl value 397 | — | — | — | — | — |
| | Polymer polyol | Hydroxyl value 27 | — | — | — | — | — |
| | Polyester polyol (ethylene adipate-based) | Hydroxyl value 56 | — | — | — | — | — |
| | Polycarbonate polyol | Hydroxyl value 55 | — | — | — | — | — |
| Crosslinking agent | Diethylene glycol | — | 18 | 18 | 18 | 18 | — |
| | Ethylene glycol | — | — | — | — | — | 10.5 |
| Isocyanate | Polyol-modified MDI | NCO% 28.0 | — | — | — | — | 82.5 |
| | Monomeric MDI | NCO% 33.6 | 61.9 | — | — | — | — |
| | Polyol-modified MDI | NCO% 23.1 | — | 101.9 | 76.6 | — | — |
| | Polymeric MDI | NCO% 30.7 | — | — | — | 82.0 | — |
| | Carbodiimide-modified MDI | NCO% 28.7 | — | — | — | — | — |
| Modifier | Water | — | 7 | 7 | 7 | 7 | 7 |
| Diluting solvent | Tetrahydrofuran | — | 267 | 267 | 267 | 267 | 267 |
| Type of substrate | | | PP | PP | PP | PP | PP |
| Spin coating condition | | | 5000 rpm for 1 minute | 5000 rpm for 1 minute | 5000 rpm for 1 minute | 5000 rpm for 1 minute | 5000 rpm for 1 minute |
| Curing conditions (atmosphere) | Formation of pores | | at 40°C for 30 minutes (Water vapor) | at 40°C for 30 minutes (Water vapor) | at 40°C for 30 minutes (Water vapor) | at 40°C for 30 minutes (Water vapor) | at 40°C for 30 minutes (Water vapor) |
| | Acceleration of curing | | at 60°C overnight (Dry) | at 60°C overnight (Dry) | at 60°C overnight (Dry) | at 60°C overnight (Dry) | at 60°C overnight (Dry) |
| Membrane thickness at the crest ($\mu m$) | | | 3 | 6 | 4 | 4 | 4 |
| Average size of top surface pore ($\mu m$) | | | 0.9 | 6.7 | 2.2 | 0.8 | 2.2 |

Fig.26

| | | Sample 24 | Sample 25 |
|---|---|---|---|
| | | Through-hole membrane | Non-through-hole membrane |
| Polyol | Polyether | 100 parts by mass (4.9999g) | 100 parts by mass (4.9999g) |
| Crosslinking agent | Diethylene glycol | 18.1 parts by mass (0.9019g) | 18.1 parts by mass (0.9019g) |
| Modifier | Water | 6.7 parts by mass (350 μL: 0.3588g) | 6.7 parts by mass (350 μL: 0.3588g) |
| Isocyanate | Polyol-modified MDI | 82.4 parts by mass (4.1427g) | 82.4 parts by mass (4.1427g) |
| Diluting solvent | Tetrahydrofuran | 267 parts by mass (15mL) | 267 parts by mass (15mL) |
| Type of substrate | | PP | PP |
| Spin coating condition | | room temperature, 5000 rpm for 1 minute | room temperature 5000 rpm for 1 minute |
| Curing conditions (atmosphere) | Formation of pores | at 40°C for 30 minutes (Water vapor) | at 40°C for 30 minutes (Water vapor) |
| | Acceleration of curing | at 60°C overnight (Dry) | at 60°C overnight (Dry) |
| Time between mixing and spin coating | | 12 minutes | 30 minutes |
| Membrane thickness at the crest ($\mu$m) | | 6 | 3 |
| Average size of top surface pore ($\mu$m) | | 14 | 3 |
| Average size of bottom surface pore ($\mu$m) | | 11 | — |

POLYURETHANE POROUS MEMBRANE

Fig.33

| | | Sample 26 | Sample 27 | Sample 28 |
|---|---|---|---|---|
| | | Porous top surface and non-porous bottom surface | | Non-porous |
| Polyol | Polyether | 100 parts by mass (5.0042g) | 100 parts by mass (10.0078g) | 100 parts by mass (5.0107g) |
| Crosslinking agent | Diethylene glycol | 18.1 parts by mass (0.9052g) | 18.1 parts by mass (1.8156g) | 18.1 parts by mass (0.9004g) |
| Modifier | Water | 6.7 parts by mass (350 μL:0.3660g) | 6.7 parts by mass (700 μL:0.7308g) | 6.7 parts by mass (350 μL:0.3466g) |
| Isocyanate | Polyol-modified MDI | 82.4 parts by mass (4.1840g) | 82.4 parts by mass (8.2405g) | 82.4 parts by mass (4.1290g) |
| Diluting solvent | Tetrahydrofuran | 91.5 parts by mass (15mL) | 95.9 parts by mass (10mL) | 268.3 parts by mass (15mL) |
| Type of substrate | | PET | PET | PET |
| Spin coating condition | | room temperature 5000 rpm for 1 minute | room temperature 5000 rpm for 1 minute | room temperature 2000 rpm for 1 minute |
| Curing conditions (atmosphere) | Formation of pores | at 40°C for 30 minutes (Water vapor) | at 40°C for 30 minutes (Water vapor) | — |
| | Acceleration of curing | at 60°C overnight (Dry) | at 60°C overnight (Dry) | at 60°C overnight (Dry) |
| Membrane thickness at the crest (μm) | | 9 | 14 | 6 |
| Average size of top surface pore (μm) | | 16.2 | 11.1 | — |

PRODUCTION METHOD OF POLYURETHANE POROUS MEMBRANE TO BE USED FOR AT LEAST ONE OF APPLICATIONS OF CELL CULTURE AND CANCER CELL GROWTH INHIBITION

CROSS REFERENCE TO RELATED APPLICATIONS

The present application claims priority from Japanese patent application P2013-143371 filed on Jul. 9, 2013 and P2014-104225 filed on May 14, 2014, the entirety of disclosure of which is hereby incorporated by reference into this application.

FIELD

The present invention relates to a production method of a polyurethane porous membrane to be used for at least one of applications of cell culture and cancer cell growth inhibition.

DESCRIPTION OF RELATED ART

Cell culture technology has lately drawn attention as the useful technology in various fields including drug discovery and regenerative medicine. A substrate serving as cell scaffold is used for culture of anchorage-dependent cells. With respect to the substrate used for cell culture, the minute physical structure as well as the chemical properties on the surface of the substrate are important as is known in the art. One of known substrates is a substrate which is made of a polymer material and has minute irregularities on the surface. Various techniques may be employed to provide the substrate made of the polymer material with minute irregularities: for example, condensation technique, nanoimprint technique, lithography or emulsion technique (for example, JP 2009-242495A).

SUMMARY

The prior art production methods of a cell culture substrate are, however, all rather complicated and need a number of steps and accordingly have difficulty in reducing the manufacturing cost. Additionally, the prior art methods generally have difficulty in producing a porous membrane with pores passing through to the bottom surface. In the case of cell culture using a porous membrane with through holes, both the top surface and the bottom surface of the porous membrane can be used for cell culture. For example, different types of cells may be cultured on the top surface and on the bottom surface. This may expand the application of cell culture technology. For this purpose, there has been a need for development of a cell culture sheet with through holes. Especially, there have been no known production methods of a porous membrane for cell culture with through holes having the pore diameter of less than 10 μm. Since the standard cell size is about 10 μm, using the porous membrane with the through holes having the pore diameter of less than 10 μm is expected to allow for analysis of the interaction between different types of cells. There is accordingly a need for development of a porous membrane with through holes having the pore diameter of less than 10 μm.

Some of the porous membranes having minute irregularities formed on the top surface have been known to have the effect of cell growth inhibition (for example, JP 2005-152526A). The porous membrane having the effect of cancer cell growth inhibition as one example of the effect of cell growth inhibition is expected to be used for cancer treatment, for suppression of cancer recurrence or cancer metastasis, or for cancer research. There is accordingly a need to produce a porous membrane having such effect of cell growth inhibition by a simple manufacturing process.

In order to solve at least part of the problems described above, the present invention may be implemented by the following aspects and embodiments.

(1) According to one aspect, there is provided a production method of a polyurethane porous membrane to be used for at least one of applications of cell culture and cancer cell growth inhibition. This production method of the polyurethane porous membrane comprises: a first step of forming a layer of a polyurethane material which is uncured, on a substrate; and a second step of supplying water vapor to an exposed surface of the layer of the polyurethane material formed on the substrate, which is away from the substrate, so as to cure the polyurethane material and provide the layer of the polyurethane material with a porous structure having a plurality of irregularities on the exposed surface.

The production method of the polyurethane porous membrane to be used for at least one of the applications of cell culture and cancer cell growth inhibition according to this aspect produces the polyurethane porous membrane to be used for at least one of the applications of cell culture and cancer cell growth inhibition by the simple process of supplying the water vapor to the polyurethane material layer. This advantageously reduces the manufacturing cost of the polyurethane porous membrane.

(2) According to one embodiment of the production method of the polyurethane porous membrane to be used for at least one of the applications of cell culture and cancer cell growth inhibition described in (1), the porous structure of the polyurethane porous membrane provided at the second step may be comprised of a plurality of pores open to the exposed surface, and only a single pore may be present in a membrane thickness direction of the polyurethane porous membrane. The production method of the polyurethane porous membrane according to this embodiment enables production of the polyurethane porous membrane suitable for at least one of the applications of cell culture and cancer cell growth inhibition.

(3) According to another embodiment of the production method of the polyurethane porous membrane to be used for at least one of the applications of cell culture and cancer cell growth inhibition described in (2), the polyurethane porous membrane may have a thickness of 0.1 to 100 μm. The production method of the polyurethane porous membrane according to this embodiment enables production of the polyurethane porous membrane suitable for at least one of the applications of cell culture and cancer cell growth inhibition.

(4) According to another embodiment of the production method of the polyurethane porous membrane to be used for at least one of the applications of cell culture and cancer cell growth inhibition described in (3), the thickness of the polyurethane porous membrane may be controlled to 0.1 to 100 μm by regulating a condition selected from a composition of the polyurethane material formed to the layer at the first step, a reaction temperature at the second step and a reaction time at the second step. The production method of the polyurethane porous membrane according to this embodiment enables the polyurethane porous membrane suitable for at least one of the applications of cell culture and cancer cell growth inhibition to be readily produced.

(5) According to another embodiment of the production method of the polyurethane porous membrane to be used for at least one of the applications of cell culture and cancer cell growth inhibition described in (2), the polyurethane porous membrane may have an average pore diameter of 0.1 to 100 μm on the exposed surface. The production method of the polyurethane porous membrane according to this embodiment enables production of the polyurethane porous membrane suitable for at least one of the applications of cell culture and cancer cell growth inhibition.

(6) According to another embodiment of the production method of the polyurethane porous membrane to be used for at least one of the applications of cell culture and cancer cell growth inhibition described in (5), the average pore diameter on the exposed surface of the polyurethane porous membrane may be controlled to 0.1 to 100 μm by regulating a condition selected from a reaction temperature at the second step, a reaction time at the second step and an amount of the water vapor supplied to the exposed surface at the second step. The production method of the polyurethane porous membrane according to this embodiment enables the polyurethane porous membrane suitable for at least one of the applications of cell culture and cancer cell growth inhibition to be readily produced.

(7) According to another embodiment of the production method of the polyurethane porous membrane to be used for at least one of the applications of cell culture and cancer cell growth inhibition described in any of (1) to (6), the porous structure provided at the second step may be comprised of a plurality of pores open to the exposed surface, and at least part of the plurality of pores may be made as pores passing through to a surface of the layer of the polyurethane material adjacent to the substrate. The production method of the polyurethane porous membrane according to this embodiment enables production of the polyurethane porous membrane suitable for at least one of the applications of cell culture and cancer cell growth inhibition. This also provides a polyurethane porous membrane having both surfaces usable as the cell culture scaffolds. Using such a polyurethane porous membrane allows for cell culture which provides an interaction between cells cultured on the respective surfaces.

(8) According to another embodiment of the production method of the polyurethane porous membrane to be used for at least one of the applications of cell culture and cancer cell growth inhibition described in (7), at least part of the plurality of pores may be made as the pores passing through to the surface of the layer of the polyurethane material adjacent to the substrate by regulating a condition selected from a composition of the polyurethane material formed to the layer at the first step, a reaction temperature at the second step and a reaction time at the second step. The production method of the polyurethane porous membrane according to this embodiment enables production of the polyurethane porous membrane suitable for at least one of the applications of cell culture and cancer cell growth inhibition. This also provides a polyurethane porous membrane having both surfaces usable as the cell culture scaffolds. Using such a polyurethane porous membrane allows for cell culture which provides an interaction between cells cultured on the respective surfaces.

(9) According to another embodiment of the production method of the polyurethane porous membrane to be used for at least one of the applications of cell culture and cancer cell growth inhibition described in (7), the first step may comprise: a mixing step of mixing the polyurethane material including at least a polyol and an isocyanate; and a layer formation step of forming the polyurethane material mixed in the mixing step to the layer. At least part of the plurality of pores may be made as the pores passing through to the surface of the layer of the polyurethane material adjacent to the substrate by regulating a condition selected from a time between the mixing step and the layer formation step and an environment temperature of the polyurethane material between the mixing step and the layer formation step. The production method of the polyurethane porous membrane according to this embodiment enables production of the polyurethane porous membrane suitable for at least one of the applications of cell culture and cancer cell growth inhibition.

(10) According to another embodiment of the production method of the polyurethane porous membrane to be used for at least one of the applications of cell culture and cancer cell growth inhibition described in any of (1) to (9). The production method of the polyurethane porous membrane may further comprise a third step of further curing the polyurethane material with stopping the supply of the water vapor, after the second step. The production method of the polyurethane porous membrane according to this embodiment provides a polyurethane porous membrane having a smaller average pore diameter on the exposed surface and a smaller variation in pore diameter of the pores open to the exposed surface.

(11) According to another aspect, there is provided a polyurethane porous membrane produced by the production method of the polyurethane porous membrane to be used for at least one of the applications of cell culture and cancer cell growth inhibition described in any of (1) to (10). The polyurethane porous membrane has a first surface and a second surface, which is opposite to the first surface, and has a porous structure comprised of a plurality of pores. Each of the pores is open to the first surface and has a curved inner wall surface that is convex toward the second surface. At least part of the plurality of pores may be made as pores passing through to the second surface.

The invention may be implemented by various aspects other than the production method described above: for example, a polyurethane porous membrane produced by the production method of the polyurethane porous membrane to be used for at least one of the applications of cell culture and cancer cell growth inhibition, and a method of specifying a composition of a polyurethane material for production of the polyurethane porous membrane to be used for at least one of the applications of cell culture and cancer cell growth inhibition.

The production method of the polyurethane porous membrane to be used for at least one of the applications of cell culture and cancer cell growth inhibition of the invention produces the polyurethane porous membrane by the simple process of supplying the water vapor to the polyurethane material layer. This advantageously reduces the manufacturing cost of the polyurethane porous membrane.

BRIEF DESCRIPTION OF DRAWINGS

FIG. 8 is a chart showing the material compositions and the curing conditions of polyurethane membranes;

FIG. 9 is a chart showing the results of observation of the polyurethane membranes;

FIG. 10 is a chart showing the material compositions and the curing conditions of polyurethane membranes;

FIG. 11 is a chart showing the results of observation of the polyurethane membranes;

FIG. 12 is a chart showing the material compositions and the curing conditions of polyurethane membranes;

FIG. 13B is a chart showing the results of observation of the polyurethane membranes;

FIG. 14 is a chart showing the material compositions and the curing conditions of polyurethane membranes;

FIG. 15A is a chart showing the results of observation of the polyurethane membranes;

FIG. 15B is a chart showing the results of observation of the polyurethane membranes;

FIG. 16A is a chart showing the material compositions and the curing conditions of polyurethane membranes and the measurement results;

FIG. 16B is a chart showing the material compositions and the curing conditions of polyurethane membranes and the measurement results;

FIG. 26 is a chart showing the material compositions and the curing conditions of polyurethane membranes and the measurement results;

FIG. 33 is a chart showing the material compositions and the curing conditions of polyurethane membranes and the measurement results;

DESCRIPTION OF EMBODIMENTS

A. Structure of Polyurethane Porous Membrane

Figure 1:
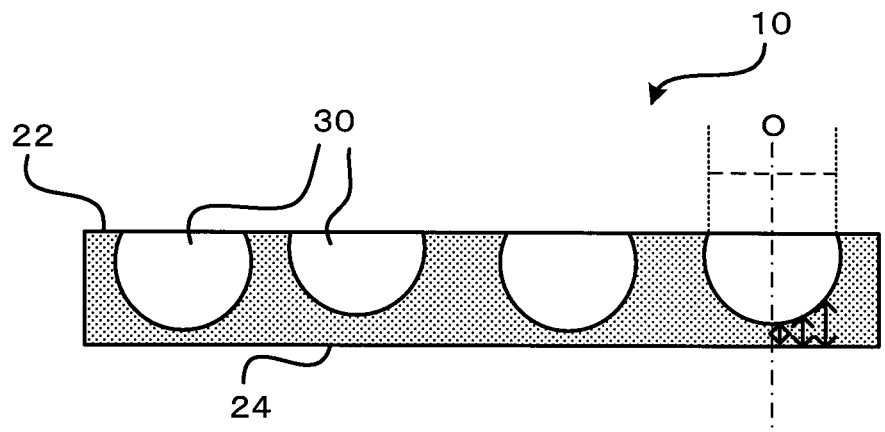
FIG. 1 is a cross sectional view schematically illustrating the structure of an exemplified polyurethane porous membrane.

FIG. 1 is a cross sectional view schematically illustrating the structure of a polyurethane porous membrane 10 as an exemplified membrane produced by the production method of the polyurethane porous membrane according to one embodiment of the invention. The polyurethane porous membrane 10 is made of polyurethane and has a plurality of pores 30. The polyurethane porous membrane has a top surface 22 as a first surface and a bottom surface 24 as a second surface, where the plurality of pores 30 are all open to the top surface 22. The average pore diameter of the pores 30 on the top surface 22 is, for example, 0.1 to 100 μm.

As illustrated in FIG. 1, only a single pore 30 is present in the membrane thickness direction of the polyurethane porous membrane 10. The inner wall of the pore 30 is generally formed to be a substantially curved surface. The inner wall surface of the pore 30 may, however, not be necessarily the smooth surface but may have a plurality of minute irregularities. The minute irregularities formed on the inner wall surface of the pore 30 are, for example, the irregularities having the widths of not greater than 20% of the membrane thickness or preferably the irregularities having the widths of not greater than 10% of the membrane thickness. The pore 30 is open to the top surface 22 and has a curved inner wall surface that is convex toward the bottom surface 24. More specifically, the distance from the bottom surface 24 to the bottom of the inner wall surface of the pore 30 on the side closer to the bottom surface 24 than the top surface 22 gradually decreases with a decrease in distance to the center axis of the pore 30 in the cross section parallel to the membrane thickness direction of the polyurethane porous membrane 10. In FIG. 1, the center axis of the pore 30 in the cross section parallel to the membrane thickness direction of the polyurethane porous membrane 10 is shown as center axis O. The state that the distance between the bottom of the pore 30 and the bottom surface 24 decreases with a decrease in distance to this center axis O is shown by arrows.

Figure 2:
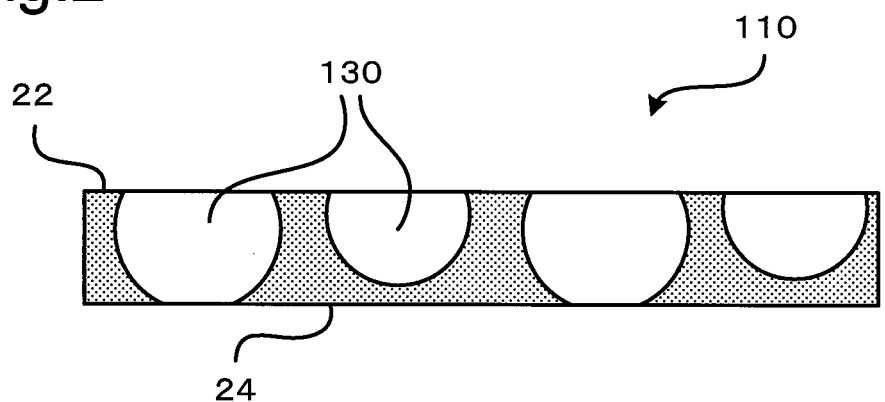
FIG. 2 is a cross sectional view schematically illustrating the structure of another exemplified polyurethane porous membrane.

FIG. 2 is a cross sectional view schematically illustrating the structure of a polyurethane porous membrane 110 as another exemplified membrane produced by the production method of the polyurethane porous membrane according to the embodiment of the invention. In the polyurethane porous membrane 110, the components similar to those of the polyurethane porous membrane 10 are expressed by the same reference numbers and are not specifically described here. The polyurethane porous membrane 110 has a plurality of pores 130, instead of the plurality of pores 30. The pore 130 has a similar shape to that of the pore 30 but differs from the pore 30 by the structure that at least part of the plurality of pores 130 pass through to the bottom surface 24. The distance from the bottom surface 24 to the bottom of the pore 130 gradually decreases with a decrease in distance to the center axis of the pore 130 in the cross section parallel to the membrane thickness direction of the polyurethane porous membrane 110, and reaches zero at the locations where the pore 130 passes through to the bottom surface 24. The average pore diameter of the pores 130 on the top surface 22 of the polyurethane porous membrane 110 is, for example, 0.1 to 100 μm.

Figure 3:
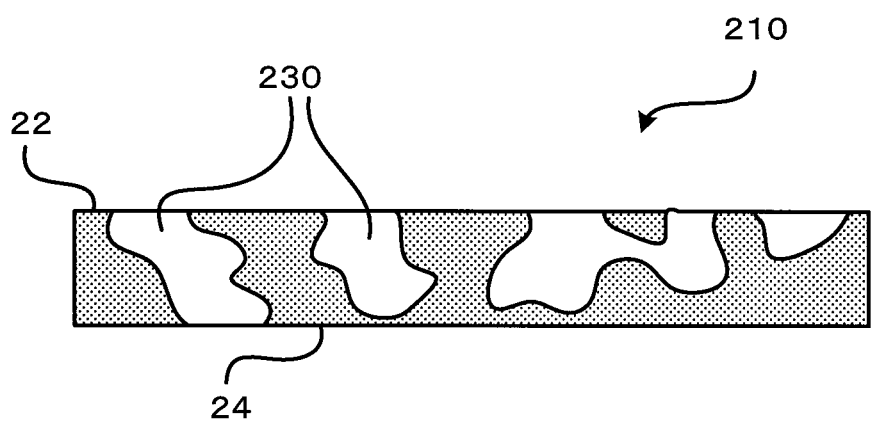
FIG. 3 is a cross sectional view schematically illustrating the structure of yet another exemplified polyurethane porous membrane.

FIG. 3 is a cross sectional view schematically illustrating the structure of a polyurethane porous membrane 210 as yet another exemplified membrane produced by the production method of the polyurethane porous membrane according to the embodiment of the invention. In the polyurethane porous membrane 210, the components similar to those of the polyurethane porous membrane 10 are expressed by the same reference numbers and are not specifically described here. The polyurethane porous membrane 210 has a plurality of pores 230, instead of the plurality of pores 30. The pores 230 have no definite shape.

As describes above, the polyurethane porous membrane produced by the production method of the polyurethane porous membrane according to the embodiment of the invention may have irregularities different from those of the polyurethane porous membranes 10 and 110 described above on at least the top surface 22. In any case, the membrane thickness of the polyurethane porous membrane is, for example, 0.1 to 100 μm. The membrane thickness of the polyurethane porous membrane denotes the distance between the highest position of the convex in the irregularities formed on the top surface 22 of the polyurethane porous membrane and the bottom surface 24 (i.e., the distance between the highest position of the convex and a substrate since the polyurethane porous membrane is formed on the substrate according to the embodiment as described later). In the description hereinafter, this membrane thickness is called "membrane thickness at the crest". In the description hereinafter, the distance between the deepest position of the concave in the irregularities formed on the top surface 22 of the polyurethane porous membrane and the bottom surface 24 (i.e., the distance between the deepest position of the concave and the substrate) is called "membrane thickness at the trough". With respect to the membrane produced by the production method of the polyurethane porous membrane according to the embodiment of the invention, the membrane thickness at the trough is preferably not greater than 95%, more preferably not greater than 85% and furthermore preferably not greater than 50% of the membrane thickness at the crest. The membrane thickness at the trough may be equal to 0% (this means that pores pass through the membrane).

The membrane thickness at the crest and the membrane thickness at the trough of the polyurethane porous membrane are determined by observing the cross section of the polyurethane porous membrane with a scanning electron microscope (SEM). For example, a concrete procedure may select three visual fields in a SEM image of the cross section of the polyurethane porous membrane, measures the membrane thicknesses at five different locations selected at random in each visual field, calculates an average value of the measurement values in each visual field and determines a mean value of the average values of the respective visual fields.

The average pore diameter of the polyurethane porous membrane is determined by observing the surface of the polyurethane porous membrane with the scanning electron microscope (SEM). For example, a concrete procedure measures the maximum length with respect to all the pores observed in a specific visual field on a SEM image of the surface of the polyurethane porous membrane and determines an average value of the measurement values. The maximum length denotes a maximum value of the side lengths of a rectangle circumscribing a pore.

The polyurethane porous membrane according to the embodiment described above may be used as a cell culture substrate which provides cell culture scaffolds by utilizing the surface with the irregularities (for example, the top surface which the pores are open). One example of the application that the polyurethane porous membrane of the embodiment is used as the cell culture scaffolds is a cell chip application having the cell response stabilized by arraying the cells or patterning the cells to equalize the cell distribution. Another example is an application in the regenerative medical field that the polyurethane porous membrane is used as the cell scaffolds in production of artificial tissues, such as artificial blood vessels to be coated with the cells constituting the blood vessels.

The polyurethane porous membrane having the pores passing through to the bottom surface may be used for cell culture by utilizing both surfaces of the membrane. In this case, different types of cells may be cultured on the top surface and the bottom surface, and the interaction between the different types of cells may be evaluated. Especially when the pore diameter (average pore diameter) of the pores passing through to the bottom surface is less than 10 μm which is the standard cell size, the interaction between different types of cells can be analyzed specifically with the higher accuracy by allowing for transfer of substances (for example, secretions from the respective cells) while interfering with migration of cells between the top surface and the bottom surface.

The polyurethane porous membrane of the embodiment may be used for an application of cancer cell growth inhibition, in addition to or in place of the application of cell culture. For example, the polyurethane porous membrane may be used for cancer treatment, for suppression of cancer recurrence or cancer metastasis, or for cancer research. In the application of the polyurethane porous membrane for cancer treatment or for suppression of cancer recurrence or cancer metastasis, the polyurethane porous membrane preferably has the pores 30 with the bottoms away from the bottom surface 24 of the polyurethane porous membrane, like the polyurethane porous membrane 10 shown in FIG. 1. The polyurethane porous membrane may be placed in the body, such that the top surface 22 with the irregularities is in contact with cancer cells or is in contact with tissues of interest as the object of suppressing cancer cell growth. This suppresses migration of the cancer cells from the top surface 22 to the bottom surface 24 through the through holes in the polyurethane porous membrane. When the polyurethane porous membrane is used for the purpose of cancer cell growth inhibition as described above, an anticancer drug may additionally be provided on at least one of the top surface 22 and the bottom surface 24 of the polyurethane porous membrane.

B. Production Method of Polyurethane Porous Membrane

Figure 4:
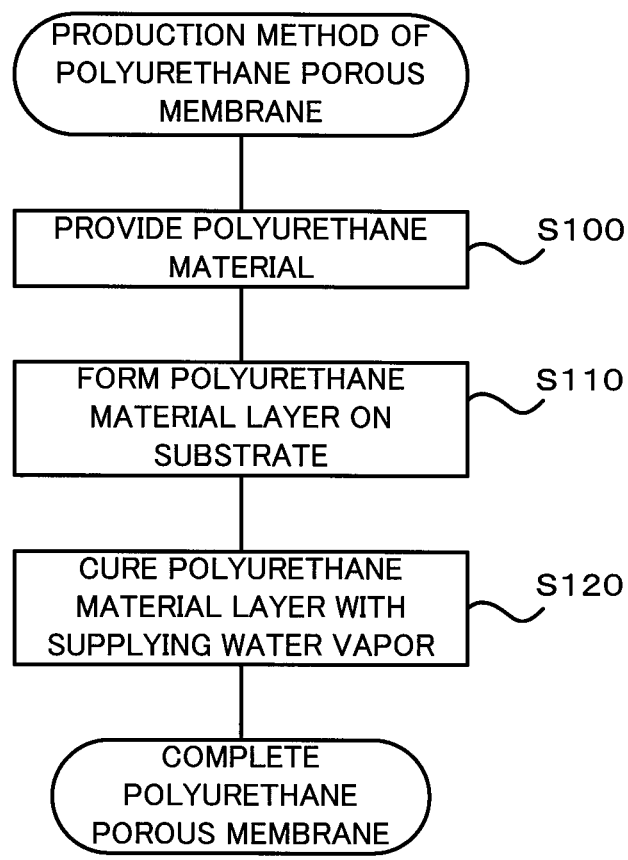
FIG. 4 is a flowchart showing a production method of the polyurethane porous membrane.

FIG. 4 is a flowchart showing a production method of the polyurethane porous membrane according to the embodiment of the invention. The production method of the polyurethane porous membrane first provides an uncured polyurethane material (step S100). The polyurethane material includes a polyol or polyhydric alcohol, an isocyanate and a diluting solvent. The step of mixing the respective components constituting the polyurethane material corresponds to the "mixing step" described in Solution to Problem.

The polyol used may be a known polyol and is, for example, a polyol having hydroxyl value of 20 to 570. The number of functional groups of the polyol is preferably two or more, in order to continue the good reaction with the isocyanate. The number of functional groups of the polyol is preferably eight or less, in order to make the reaction of pore formation proceed well. The number-average molecular weight of the polyol is preferably not less than 100 and is more preferably not less than 1000, in order to ensure the flexibility of the polyurethane porous membrane. The number-average molecular weight of the polyol is also preferably not greater than 20000 and is more preferably not greater than 10000, in order to reduce the viscosity of the polyurethane material. Available examples of the polyol include polyether polyol, polymer polyol, polyester polyol, acrylic polyol and polycarbonate polyol. Any of these polyols may be used alone or two or more of these polyols may be used in combination. Among them, polyether polyol and polymer polyol are preferable; and polyether polyol is especially preferable.

The polyether polyol used may be, for example, polypropylene ethylene polyol and/or polytetramethylene ether glycol. Especially preferable is polypropylene ethylene polyol. The polymer polyol preferably used is a polymer produced by polymerizing an unsaturated ethylene monomer such as styrene or acrylonitrile in the polyether polyol.

The isocyanate used may be a known isocyanate and is, for example, an isocyanate containing 15 to 50% by mass of isocyanate group (NCO) at the molecular end. More specifically, the isocyanate used may be selected from, for example, aromatic isocyanates and aliphatic isocyanates. Especially preferable are aromatic isocyanates. Available examples of the aromatic isocyanate include diphenylmethane diisocyanate (MDI), tolylene diisocyanate (TDI) and mixtures thereof. Among them, diphenylmethane diisocyanate (MDI) is preferable.

The MDI used may be, for example, a monomeric MDI having two isocyanate groups and two benzene rings in one molecule, a polymeric MDI having three or more isocyanate groups and three or more benzene rings in one molecule, or a mixture thereof. The MDI used is not limited to the monomeric MDI and/or the polymeric MDI but may be an MDI prepolymer obtained by reaction of MDI with a polyol.

The diluting solvent is used to adjust the viscosity of the material including the polyol and the isocyanate and is preferably a solvent that does not substantially react with the other components of the polyurethane material. The diluting solvent is also preferably a solvent that dissolves the polyol and the isocyanate to prepare the homogeneous polyurethane material. The diluting solvent used may be selected from, for example, tetrahydrofuran, acetone and methyl ethyl ketone. Tetrahydrofuran is especially preferable.

In the production method of the polyurethane porous membrane according to the embodiment, the polyurethane material provided at step S100 may additionally include water as a modifier. Water added as the modifier to the polyurethane material serves to improve the wettability of the polyurethane material to the substrate for formation of the polyurethane porous membrane. More specifically, water as the modifier serves to avoid clumping of the polyurethane material in the process of dropping or applying the polyurethane material on the substrate at step S110 described later and facilitate formation of a homogeneous polyurethane material layer on the substrate. In terms of ensuring the wettability of the polyurethane material to the substrate, the amount of water added to the polyurethane material is preferably not less than 3 parts by mass and is more preferably not less than 5 parts by mass relative to 100 parts by mass of the polyol. It is also preferable that water added as the modifier to the polyurethane material is mostly volatilized and lost before a curing step described later. The amount of water added to the polyurethane material is thus preferably not greater than 15 parts by mass and is more preferably not greater than 10 parts by mass relative to 100 parts by mass of the polyol. As long as a polyurethane material layer can be formed without any difficulty at step S120 described later, water may not be added to the polyurethane material.

Additionally, in the production method of the polyurethane porous membrane according to the embodiment, a hydroxyl group-containing compound having the lower molecular weight than that of the polyol described above (for example, molecular weight of 60 to 500 or preferably molecular weight of 60 to 300) may be added as a crosslinking agent to the polyurethane material provided at step S100. Available examples of the crosslinking agent include: diols such as ethylene glycol, diethylene glycol, 1,2-propanediol, 1,3-propanediol, 1,2-butanediol, 1,3-butanediol and 1,4-butanediol; diol compounds such as diethanolamine; triols such as glycerol; and triol compounds such as triethanolamine and trimethylolpropane.

In the production method of the polyurethane porous membrane according to the embodiment, a catalyst for accelerating curing and foaming may be added to the polyurethane material provided at step S100. The catalyst used may be a known catalyst and is, for example, a catalyst selected from amine catalysts such as triethylamine, tripropylamine and tributylamine and organometallic catalysts such as organotin compounds. Additionally, any of various known additives and auxiliaries including foam stabilizers such as surfactants, coloring agents, antioxidants such as oxidation inhibitors and ultraviolet absorbers, fillers such as calcium carbonate and barium sulfate, fire retardants, plasticizers and mold release agents may be added as appropriate. The simpler composition of the polyurethane material (i.e., the less number of components included in the polyurethane material), however, preferably relieves the potential effects on the cells described later. Additionally, it is preferable not to add the catalyst for accelerating curing, since this causes the slow progress of the foaming reaction and facilitates controlling the pore diameter.

After providing the polyurethane material at step S100, the production method forms a polyurethane material layer on a substrate (step S110). This step S110 corresponds to the "layer formation step" described in Solution to Problem, and steps S100 and S110 correspond to the "first step" described in Solution to Problem. The substrate used at step S110 may be any substrate that does not substantially react with the polyurethane material, is stable under temperature conditions in the process of producing the polyurethane porous membrane and has sufficiently smooth surface on which the polyurethane material layer is formed. The substrate used may be a film made of a material selected from polypropylene (PP), fluororesin such as polytetrafluoroethylene (PTFE), polyethylene terephthalate (PET), polyethylene, polyvinylidene chloride, polyamide and polyimide.

Figure 5:
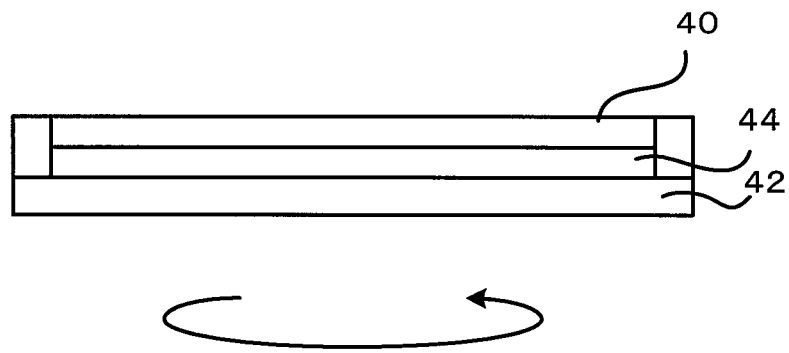
FIG. 5 is a diagram illustrating a process of forming a polyurethane material layer on a substrate.

FIG. 5 is a diagram illustrating one exemplified process of forming a polyurethane material layer 40 on a substrate 44. The method employed at step S110 to form a polyurethane material layer on the substrate is, for example, a method of dropping the polyurethane material on the substrate and forming a membrane of the polyurethane material using a spin coater, a bar coater or a lip coater, a spray coating method or a roll coating method. FIG. 5 illustrates the process of forming the polyurethane material layer by the spin coating method using a spin coater. More specifically, FIG. 5 illustrates a process of forming the polyurethane material layer 40 on the substrate 44 fastened on a glass plate 42 placed on a turn table of the spin oater. In the description hereof, in the case of forming the polyurethane material layer on the substrate to produce a polyurethane membrane, an exposed surface of the resulting polyurethane membrane away from the substrate is called "top surface", and an opposite surface adjacent to the substrate is called "bottom surface".

The thickness of the polyurethane material layer formed at step S110 is, for example, 0.1 to 20 µm. In order to ensure the strength of the polyurethane porous membrane and improve the handling ability, the thickness of the polyurethane material layer is preferably not less than 1 µm and is more preferably not less than 3 µm. In order to obtain the polyurethane porous membrane having the pores passing through to the opposite surface adjacent to the substrate at step S120 described later, the thickness of the polyurethane material layer is preferably not greater than 15 µm and is more preferably not greater than 10 µm.

The diluting solvent included in the polyurethane material is generally highly volatile, so that the diluting solvent is rapidly volatilized from the formed polyurethane material layer when the polyurethane material layer is formed at step S110. The thickness of the polyurethane material layer formed at step S110 accordingly decreases with an increase in ratio of the diluting solvent included in the polyurethane material used for formation of the polyurethane material layer at step S110. It is also preferable that water included in the polyurethane material layer is sufficiently volatilized at step S110, prior to step S120 of curing polyurethane described later. More specifically, it is preferable to reduce the amount of water included in the polyurethane material layer to such a level that water in the polyurethane material does not substantially serve as the foaming agent at step S120 of curing polyurethane described later. When the spin coating method is employed at step S110 to form the polyurethane material layer, the diluting solvent and water can be volatilized simultaneously with formation of the layer of the polyurethane material.

After forming the polyurethane material layer at step S110, the production method cures the polyurethane material layer with supplying the water vapor to the polyurethane material layer (step S120), so as to complete the polyurethane porous membrane. This produces, for example, the polyurethane porous membranes 10, 110 and 210 shown in FIGS. 1 to 3. This step S120 corresponds to the "second step" described in Solution to Problem.

More specifically, the production method cures the polyurethane material with supplying water vapor to the exposed surface of the polyurethane material layer 40 away from the substrate 44. The method employed to supply water vapor to the exposed surface of the polyurethane material layer 40 is, for example, a method of placing the polyurethane material layer 40 formed on the substrate 44 under an environment of saturated vapor pressure. Another available method sprays the water vapor to the exposed surface of the polyurethane material layer using, for example, a water vapor spray nozzle.

Figure 6:
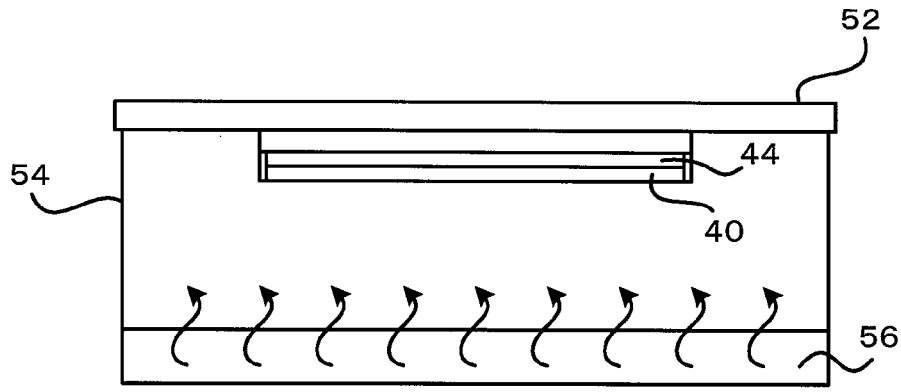
FIG. 6 is a diagram illustrating a process of curing polyurethane with supplying water vapor.

FIG. 6 is a diagram schematically illustrating a process of placing the polyurethane material layer 40 under the environment of saturated vapor pressure to produce the polyurethane porous membrane. This process uses an airtight container 54 with a cover member 52 and applies the substrate 44 to the rear side of the cover member 52 with adding water 56 in the airtight container 54 to make the exposed surface of the polyurethane material layer 40 opposed to the water 56. For example, the airtight container 54 is placed in a thermostatic bath set to a predefined temperature, so as to maintain the internal temperature of the airtight container 54 at the predefined temperature and control the vapor pressure in the airtight container 54 to the saturated vapor pressure at the predefined temperature. The process of supplying the water 56 in the form of water vapor to the polyurethane material layer 40 is shown by arrows in FIG. 6. The temperature of the reaction (called "reaction temperature") at step S120 denotes the temperature of the polyurethane material layer where the reaction proceeds and is equivalent to the set temperature of the thermostatic bath in which the airtight container 54 is placed in the method shown in FIG. 6. In the application using the water vapor spray nozzle as mentioned above, the reaction temperature is, for example, the temperature of the water vapor to be sprayed.

The curing reaction proceeds in the polyurethane material layer in which the polyol is mixed with the isocyanate. In the polyurethane material layer, the reaction involved in foaming proceeds on the exposed surface to which the water vapor is supplied. More specifically, in the polyurethane material layer, when the water vapor is supplied to the exposed surface, the isocyanate in the polyurethane material reacts with the water vapor to produce carbon dioxide, which foams polyurethane in the course of curing (to form pores) to make porous. According to this embodiment, the water vapor accordingly serves as the foaming agent of polyurethane. Formation of pores proceeds on the exposed surface to which the water vapor serving as the foaming agent is supplied, so that pores are generally formed to be open to the exposed surface (top surface 22) in the resulting polyurethane porous membrane as shown in FIGS. 1 to 3.

In the production method of the polyurethane porous membrane of the embodiment, the structure of the polyurethane porous membrane is controllable by regulating the condition selected from the time of the reaction at step S120 (called "reaction time"), the amount of water vapor supplied to the polyurethane material layer at step S120 (called "supply amount of water vapor") and the composition of the polyurethane material. The structure of the polyurethane porous membrane herein includes the shape of pores formed in the polyurethane porous membrane, the diameter of pores, the variation in diameter of pores and the membrane thickness of the polyurethane porous membrane.

The reaction of curing polyurethane (called "curing reaction") and the reaction of foaming polyurethane (called "foaming reaction") are both chemical reactions. An increase in reaction temperature at step S120 thus enhances the activation degree of each reaction, and an increase in reaction time at step S120 makes more progress of each reaction. Accordingly, regulating the reaction temperature and/or the reaction time at step S120 changes the balance between the curing reaction and the foaming reaction, so as to control the structure of the resulting polyurethane porous membrane. In terms of ensuring the productivity of the polyurethane porous membrane and assuring the sufficient porosity of the polyurethane membrane, the reaction temperature is preferably not lower than 20° C., is more preferably not lower than 30° C. and is furthermore preferably not lower than 40° C. In order to control the size of pores formed in the polyurethane porous membrane, the reaction temperature is preferably not higher than 120° C., is more preferably not higher than 80° C. and is furthermore preferably not higher than 60° C. The reaction time may be adequately set according to the reaction temperature. In terms of ensuring the productivity of the polyurethane porous membrane, the reaction time is preferably not longer than 24 hours, is more preferably not longer than 17 hours and is furthermore preferably not longer than 60 minutes. In terms of the assuring the sufficient porosity of the polyurethane membrane, the reaction time is preferably not shorter than 1 minute and is more preferably not shorter than 10 minutes.

The reaction temperature and the reaction time at step S120 are the important parameters to change the shape of pores formed in the resulting polyurethane porous membrane. More specifically, adequate settings of the reaction temperature and the reaction time control the shape of pores, such that the inner wall of the pore is generally formed to a substantially curved surface and the pores are open to the exposed surface of the polyurethane porous membrane. Additionally, the settings control the shape of pores, such that only a single pore is present in the membrane thickness direction (no plural pores are continuously formed in the membrane thickness direction) (FIGS. 1 and 2).

The reaction temperature and the reaction time at step S120 are also the important parameters to change the average pore diameter and the variation in pore diameter on the exposed surface (top surface 22) of the polyurethane porous membrane. The average pore diameter of the polyurethane porous membrane is controllable in the range of 0.1 to 100 μm by regulating the reaction temperature and/or the reaction time. In order to control the average pore diameter in the above range, the reaction temperature is preferably not lower than 20° C., is more preferably not lower than 30° C. and is furthermore preferably not lower than 40° C. In order to control the average pore diameter in the above range, the reaction temperature is also preferably not higher than 120° C., is more preferably not higher than 80° C. and is furthermore preferably not higher than 60° C. The reaction time may be adequately set according to the reaction temperature. In order to control the average pore diameter in the above range, the reaction time is preferably not longer than 24 hours, is more preferably not longer than 17 hours and is furthermore preferably not longer than 60 minutes. In order to control the average pore diameter in the above range, the reaction time is also preferably not shorter than 1 minute and is more preferably not shorter than 10 minutes.

The activation degree of the foaming reaction increases with an increase in reaction temperature. Setting the lower reaction temperature accordingly decreases the pore diameter (average pore diameter) of the pores formed in the resulting polyurethane porous membrane and reduces the variation in pore diameter. In order to sufficiently decrease the diameter of the pores and reduce the variation in pore diameter, the reaction temperature is preferably not higher than 55° C. and is more preferably not higher than 45° C. In terms of the production efficiency, on the other hand, the reaction temperature is preferably not lower than 35° C. and is more preferably not lower than 38° C. The average pore diameter on the exposed surface (top surface 22) of the polyurethane porous membrane is also controllable by regulating the amount of the water vapor supplied to the exposed surface of the polyurethane material layer, in addition to or in place of regulating the reaction temperature and/or the reaction time described above. This is because the activation degree of the foaming reaction increases with an increase in supply amount of the water vapor serving as the foaming agent. When the curing reaction is performed in the airtight container with addition of water as shown in FIG. 6, setting the higher temperature raises the reaction temperature and also increases the saturated vapor pressure to increase the supply amount of water vapor. This results in increasing the activation degree of the foaming reaction to increase the average pore diameter. The increased size of the pores in the polyurethane porous membrane increases with membrane thickness at the trough in the pores.

Additionally, the reaction temperature and the reaction time at step S120 are the important parameters to change the membrane thickness (membrane thickness at the crest) of the polyurethane porous membrane. The thickness of the polyurethane porous membrane is controllable in the range of 1 to 100 μm by regulating the reaction temperature and/or the reaction time. The increase in activation degree of the foaming reaction increases the membrane thickness of the resulting polyurethane porous membrane. Setting the lower reaction temperature accordingly decreases the membrane thickness of the polyurethane porous membrane. In order to control the membrane thickness of the polyurethane porous membrane in the above range, the reaction temperature is preferably not lower than 20° C., is more preferably not lower than 30° C. and is furthermore preferably not lower than 40° C. In order to control the membrane thickness of the polyurethane porous membrane in the above range, the reaction temperature is also preferably not higher than 120° C., is more preferably not higher than 80° C. and is furthermore preferably not higher than 60° C. The reaction time may be adequately set according to the reaction temperature. In order to control the membrane thickness of the polyurethane porous membrane in the above range, the reaction time is preferably not longer than 24 hours, is more preferably not longer than 17 hours and is furthermore preferably not longer than 60 minutes. In order to control the membrane thickness of the polyurethane porous membrane in the above range, the reaction time is also preferably not shorter than 1 minute and is more preferably not shorter than 10 minutes.

The membrane thickness of the polyurethane porous membrane is also controllable by regulating the composition of the polyurethane material, in addition to or in place of regulating the reaction temperature and/or the reaction time described above. More specifically, an increase in ratio of the diluting solvent included in the material decreases the thickness of the polyurethane material layer subject to the reaction at step S120, due to volatilization of the diluting solvent. This results in decreasing the membrane thickness of the resulting polyurethane porous membrane. In order to control the membrane thickness of the polyurethane porous membrane in the above range, the ratio of the diluting solvent included in the material is preferably not less than 40 parts by mass and is more preferably not less than 80 parts by pass relative to 100 parts by mass of the polyol included in the material. In order to control the membrane thickness of the polyurethane porous membrane in the above range, the ratio of the diluting solvent included in the material is also preferably not greater than 500 parts by mass and is more preferably not greater than 350 parts by mass relative to 100 parts by mass of the polyol included in the material.

During the progress of the curing reaction and the foaming reaction at step S120, the thinner polyurethane material layer makes it easier to form pores passing through to the substrate side (bottom surface). Accordingly, formation of the thinner polyurethane material layer by increasing the ratio of the diluting solvent as described above makes it easier to obtain the polyurethane porous membrane having a greater number of pores passing through to the bottom surface. In order to obtain the polyurethane porous membrane having such through holes, the ratio of the diluting solvent included in the material is preferably not less than 90 parts by mass and is more preferably not less than 150 parts by mass relative to 100 parts by mass of the polyol included in the material. In order to obtain the polyurethane porous membrane having such through holes, the ratio of the diluting solvent included in the material is also preferably not greater than 500 parts by mass and is more preferably not greater than 350 parts by mass relative to 100 parts by mass of the polyol included in the material.

The depth of the pores (or the membrane thickness at the trough described later) and/or the average pore diameter of the pores formed in the polyurethane porous membrane are controllable by regulating at least one of the conditions, i.e., the time between the "mixing step" of preparing the polyurethane material at step S100 and the "layer formation step" of forming the polyurethane material layer at step S110 and the environment temperature of the polyurethane material between the above "mixing step" and the above "layer formation step". For example, regulation of the above condition controls at least part of the pores, which are to be formed in the resulting polyurethane porous material, to be through holes passing through to the bottom surface 24 adjacent to the substrate 44.

More specifically, an increase in time between the "mixing step" and the "layer formation step" or an increase in temperature between the "mixing step" and the "layer formation step" makes more progress of the curing reaction of the mixed polyurethane material. At step S120, the more progress of the curing reaction in the polyurethane material layer makes it more difficult to form pores by supply of the water vapor. Accordingly, an increase in time between the "mixing step" and the "layer formation step" or an increase in temperature between the "mixing step" and the "layer formation step" tends to decrease the depth of pores and tends to reduce the average pore diameter. In other words, a decrease in time between the "mixing step" and the "layer formation step" or a decrease in temperature between the "mixing step" and the "layer formation step" makes it easier to form through holes as at least part of the pores which are to be formed in the polyurethane porous membrane and tends to increase the average pore diameter.

The production method of the polyurethane porous membrane according to the embodiment of the invention described above enables the polyurethane porous membrane to be used for at least one of applications of cell culture and cancer cell growth inhibition to be produced by the simple technique of supplying the water vapor to the polyurethane material layer. This results in reducing the manufacturing cost of the polyurethane porous membrane.

The production method of the polyurethane porous membrane according to the embodiment of the invention enables a plurality of pores passing through to the bottom surface to be readily formed by regulating the condition selected from the reaction temperature during the progress of the curing reaction with supply of the water vapor, the reaction time, the supply amount of water vapor and the composition of the polyurethane material. This enables both surfaces of the membrane to be used as the cell culture scaffolds. Additionally, using such a polyurethane porous membrane allows for cell culture in a specific mode that provides interactions between cells on the respective surfaces.

The production method of the polyurethane porous membrane according to the embodiment of the invention reduces the pore diameter of the pores passing through to the bottom surface (average pore diameter) to be less than 10 μm which is the standard cell size. Using this membrane allows for transfer of substances (for example, secretions from respective cells) while interfering with migration of cells between the respective surfaces, thus enabling the more detailed analysis of the interactions between cells on the respective surfaces.

The method of using water (liquid water) as the foaming agent to produce porous polyurethane has been known in the art. Mixing liquid water with the polyurethane material causes a reaction of water with isocyanate to produce carbon dioxide and foam polyurethane. This embodiment, however, differs from the prior art by using water as the foaming agent not in the state of liquid water but in the vaporized state of water vapor.

In addition to liquid water, fluorocarbons and cyclopentane have also been known in the art as the foaming agent used to produce porous polyurethane. The size of the pores formed by using liquid water or fluorocarbon is generally about several hundred μm. Using liquid water or fluorocarbon accordingly has difficulty in meeting the requirement as the porous membrane for cell culture. Using liquid water or fluorocarbon as the foaming agent forms pores inside of the membrane and accordingly has difficulty in forming pores open to the top surface of the membrane to provide the surface of the membrane with the sufficient irregularities or in forming pores passing through to the bottom surface of the membrane. The production method of the polyurethane porous membrane of the embodiment, on the other hand, supplies the water vapor serving as the foaming agent on the exposed surface and thereby produces a membrane having the irregularities on the top surface suitable as the porous membrane to be used for at least one of applications of cell culture and cancer cell growth inhibition.

Another known technique for making polyurethane porous impregnates a sample with carbon dioxide gas, nitrogen gas or the air in the ordinary state or in the supercritical state and regulates the temperature to achieve the molten state of the gas and the polymer and thereby form fine pores. This known method, however, forms pores in the closed cell structure and accordingly has difficulty in forming pores open to the top surface of the membrane to provide the surface of the membrane with the sufficient irregularities or in forming pores passing through to the bottom surface of the membrane. This method also has difficulty in foaming with controlling the membrane thickness in a certain range. The production method of the polyurethane porous membrane of the embodiment, on the other hand, produces a porous membrane of a desired membrane thickness with having the irregularities on the top surface suitable as the porous membrane to be used for at least one of applications of cell culture and cancer cell growth inhibition.

C. Modification

Figure 7:
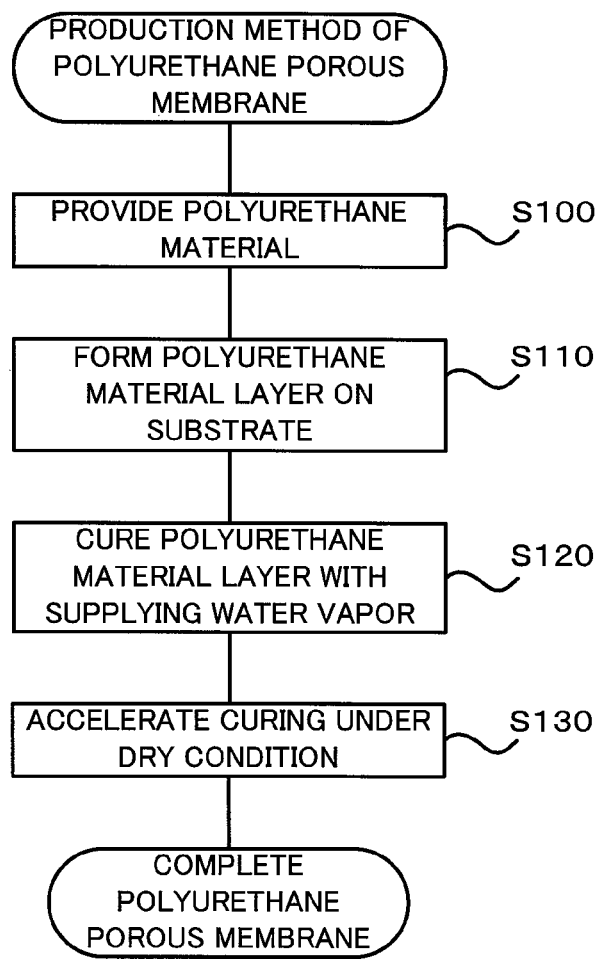
FIG. 7 is a flowchart showing another production method of the polyurethane porous membrane.

FIG. 7 is a flowchart showing a production method of a polyurethane porous membrane according to a modification of the embodiment of the invention. The steps of FIG. 7 identical with those of FIG. 4 are shown by the same step numbers and are not specifically described here. In the modified flow of FIG. 7, steps S100 to S120 are identical with those in the flow of FIG. 4. The difference from the flow of FIG. 4 is an additional step of accelerating curing of polyurethane in the dry condition with stopping the active supply of water vapor (step S130), after step S120. More specifically, when the airtight container 54 is used at step S120 as described previously, the procedure removes liquid water from the airtight container 54 and further continues the curing reaction. In another example, when the water vapor spray nozzle is used at step S120, the procedure stops the spray of water vapor using the nozzle and further continues the curing reaction.

This modified flow has the additional step of further continuing curing of polyurethane, after the step of making polyurethane porous, so that the conditions of step S120 can be set by mainly considering a desired degree of porosity. This enables the degree of porosity (more specifically, for example, the average pore diameter, the ratio of through holes passing through to the bottom surface and the degree of variation in membrane thickness due to foaming) to be controlled with the higher accuracy. Compared with the production method of FIG. 4, the production method of FIG. 7 can further decrease the average pore diameter on the top surface of the membrane and further reduce the variation in pore size by, for example, setting the lower reaction temperature and the shorter reaction time at step S120.

EXAMPLES

Preparation of Polyurethane Porous Membrane

[Samples 1 and 2]

FIG. 8 is a chart showing the material compositions and the curing conditions of polyurethane membranes of Samples 1 and 2. The polyurethane membrane of Sample 1 was produced according to the production method shown in FIG. 4. The production method of the polyurethane membrane of Sample 2 differs only by curing without supplying the water vapor at a step corresponding to step S120 of FIG. 4 as described later. The procedure of producing the polyurethane membranes of Samples 1 and 2 provided the materials of the compositions shown in FIG. 8 at step S100. As shown in FIG. 8, polyether polyol was used as the polyol in production of the polyurethane membranes of Samples 1 and 2. More specifically, the polyol used was polypropylene ethylene polyol having number-average molecular weight of about 4000 and hydroxyl value of 37. The isocyanate used as polyol-modified diphenylmethane diisocyanate (MDI) containing 28.0% by mass of isocyanate group (NCO) at the molecular end. The crosslinking agent used as diethylene glycol (DEG). The diluting solvent used as tetrahydrofuran (THF). The modified used was water or more specifically ultrapure water (Milli-Q (trademark) water). FIG. 8 shows the mass ratios of the respective components relative to 100 parts by mass of polyol and the weights of the respective components mixed as the compositions of the respective components in the materials. With regard to tetrahydrofuran, the volume of the solvent added is shown in FIG. 8. The mass ratio of tetrahydrofuran was calculated on the assumption that the concentration of tetrahydrofuran in the solvent was 0.89 g/mL.

At step S110, the procedure formed the polyurethane material layer 40 on the substrate 44 by the spin coating method shown in FIG. 5. More specifically, at step S110, the procedure added the respective components of the composition shown in FIG. 8 except the isocyanate in an airtight sample container and stirred the mixture for 30 seconds using a Vortex shaker (GENIUS3 manufactured by IKA Works Inc.) The procedure subsequently cooled down the sample container including the above mixture on an ice bath. The procedure then added a specified amount of the isocyanate shown in FIG. 8, stirred the mixture for 30 seconds using the Vortex shaker and cooled down the sample container including the mixture as the above sample on an ice bath to inhibit further reaction. The procedure again stirred the above sample for 1 minute with the Vortex shaker immediately before spin coating and applied and spin-coated 1 mL of the sample on the substrate 44 set in a spin coater. The spin coater used was MS-A100 manufactured by Mikasa Col., Ltd. The substrate 44 used was a polypropylene (PP) film and was fastened with an adhesive tape on a glass plate placed on a turn table of the spin coater. The spin coating was performed at room temperature and the rotation speed of 5000 rpm for 60 seconds.

At step S120, AIR KEEPER A-032 (capacity of 1.35 L) manufactured by Iwasaki Industry Inc. was used as the airtight container shown in FIG. 6. The procedure of producing Sample 1 added 100 mL of water in the above airtight container 54 and placed the airtight container 54 in a thermostat bath set to 40° C. which was the cure temperature to heat the airtight container 54 until the water temperature in the airtight container 54 reached the cure temperature. Immediately before starting the curing reaction, the procedure took out the airtight container 54 from the thermostat bath and wiped out the water on the rear side of the cover member 52 of the airtight container 54 with Kimtowel (registered trademark) (manufactured by Nippon Paper Crecia Co., Ltd.) to suppress the effect of water droplets during the curing reaction. The substrate 44 with the polyurethane material layer 40 formed with the spin coater was fastened to the cover member 52 by using a doubled-sided adhesive tape. The procedure closed the cover member 52 which the polyurethane material layer 40 is fixed to and placed the airtight container 54 in the thermostatic bath to heat the airtight container 54 overnight. Sample 1 was accordingly exposed to the saturated vapor pressure at 40° C. and was subject to the curing reaction at 40° C. In the description below, the atmosphere having the saturated water vapor at the cure temperature during curing of polyurethane is called water vapor atmosphere.

Sample 2 was subject to the curing step with no supply of water vapor, instead of step S120. More specifically, Sample 2 was produced by the same procedure as the procedure of producing Sample 1 described above, except that no water was added in the airtight container and the set temperature of the thermostat bath was 60° C. The water vapor pressure in the airtight container during the curing reaction of Sample 2 was accordingly equal to the water vapor pressure in the air before the airtight container was closed. In the description below, the atmosphere having the water vapor pressure without active supply of water vapor during curing of polyurethane is called dry atmosphere.

FIG. 9 is a chart showing the results of observation of the polyurethane membranes of Samples 1 and 2. The polyurethane membranes were observed at 200 to 10000-fold magnification using a scanning electron microscope (SEM, S-800 manufactured by Hitachi, Ltd.) with the accelerating voltage of 15 kV. As an example, FIG. 9 shows observation of the top surface (exposed surface away from the substrate) and the bottom surface (surface observable by removing the substrate) of the polyurethane membrane at 3000-fold magnification and observation of the cross section at 1000-fold magnification. The sample for observation of the cross section was produced by cutting the substrate 44 with the polyurethane membrane in the membrane thickness direction with a razor blade. No formation of pores was observed with regard to Sample 2 as described below, so that observation of the bottom surface by removing the substrate 44 was not performed for Sample 2.

In FIG. 9, in each sample, the membrane thickness at the crest (distance between the highest position of the convex in the irregularities formed on the top surface of the membrane) is shown as "membrane thickness at the crest". In the sample with formation of pores, the membrane thickness at the trough (distance between the deepest position of the concave in the irregularities formed on the top surface of the membrane) is shown as "membrane thickness at the trough". In the sample with formation of pores, the diameter of the opening of the pores on the top surface 22 of the membrane (refer to FIGS. 1 to 3) is shown as "size of top surface pore", and the maximum value of the diameter of the opening of the pores on the bottom surface 24 (refer to FIGS. 1 to 3) is shown as "size of maximum bottom surface pore). FIG. 9 also shows standard deviations of the "membrane thickness at the crest", the "membrane thickness at the trough" and the "size of top surface pore".

The above "membrane thickness at the crest" and the "membrane thickness at the trough" and their standard deviations were determined by selecting three visual fields in the image of the cross section of the sample, calculating an average value in each visual field and calculating a mean value of the average values of the respective visual fields. The "membrane thickness at the crest", the "membrane thickness at the trough" and their standard deviations were determined by the same procedure with regard to the other samples described later.

The "size of top surface pore" and the "size of maximum bottom surface pore" described above and the "standard deviation of the size of top surface pore" were determined by image analysis using image analysis software Mac-View (manufacture by Mountech Co., Ltd.) More specifically, the procedure of image analysis measured a maximum length (maximum value of the side lengths of a rectangle circumscribing each pore) with respect to all pores in a specific visual field (visual field at 1000-fold magnification) on the top surface or on the bottom surface of each sample and calculated an average value of the "size of top surface pore" and its standard deviation and maximum value from the measured values of maximum length. In FIG. 9, the standard deviation of the "size of top surface pore" is shown below the average value of the "size of top surface pore". With regard to the other samples described later, "size of top surface pore", "size of bottom surface pore" and their standard deviations, as well as a maximum value and a minimum value of the pore size on each of the top surface and the bottom surface were also determined by the above image analysis software.

As shown in FIG. 9, Sample 1 gave a polyurethane porous membrane having a large number of pores passing through to the bottom surface by the curing reaction under the water vapor atmosphere. No formation of pores was observed, on the other hand, in Sample 2 which employed the curing reaction under the dry atmosphere. Samples 1 and 2 had the same material compositions as shown in FIG. 8 and accordingly had almost the same thicknesses of the material layer prior to the curing reaction. Foamed Sample 1, however, had the greater membrane thickness after curing ("membrane thickness at the crest" in FIG. 9). In Sample 1, the pore diameter of the opening on the top surface 22 was greater than the pore diameter of the opening on the bottom surface 24. This indicates the progress of pore formation from the top surface 22-side to the bottom surface 24-side.

As shown in FIG. 8, each of Samples 1 and 2 contains 7 parts by mass of water relative to 100 parts by mass of polyol in the material. This content ratio is higher than a general ratio of water mixed in the material in the case of using water as the foaming agent during production of urethane foam. No formation of pores is, however, observed in Sample 2. This is attributed to that water in the material is lost in the course of spin coating and thereby water mixed in the material hardly serves as the foaming agent. In Sample 1 with formation of pores, it is thus contemplated that only the water vapor supplied to the exposed surface substantially serves as the foaming agent.

[Samples 3 to 8]

FIG. 10 is a chart showing the material compositions and the curing conditions of polyurethane membranes of Samples 3 to 8. The polyurethane membranes of Samples 3 to 8 were produced according to the production method shown in FIG. 4. More specifically, the procedure of producing the polyurethane membranes of samples 3 to 8 provided the materials of the compositions shown in FIG. 10 at step S100. As shown in FIG. 10, the polyol used to produce the polyurethane membranes of Samples 3 to 5 was polyether polyol (hydroxyl value of 37 and molecular weight of about 4000) which was the same as that of Sample 1. The polyol used to produce the polyurethane membranes of Samples 6 to 8 was, on the other hand, polymer polyol (hydroxyl value of 27 and molecular weight of about 5000, polymer obtained by graft copolymerization of styrene and acrylonitrile in polyether polyol). The types of the other components included in the material and the film formation conditions are the same as those of Sample 1. FIG. 10 shows the compositions of the respective components in the same manner as FIG. 8.

The subsequent material layer formation step of S110 and curing step of step S120 were performed in the same manner as Sample 1. The differences from Sample 1 are that the curing temperature was set to room temperature for Samples 3 and 6, the curing temperature was set to 60° C. for Samples 4 and 7 and the curing temperature was set to 80° C. for Samples 5 and 8.

FIG. 11 is a chart showing the results of observation of the polyurethane membranes of Samples 3 to 8 with the SEM in the same manner as Sample 1. As an example, FIG. 11 shows observation of the top surface (exposed surface away from the substrate) of the polyurethane membrane at 1000-fold magnification and at 5000-fold magnification. FIG. 11 also shows the overall membrane thicknesses (membrane thicknesses at the crest) of the respective samples.

As shown in FIG. 11, irregularities were formed on the top surface by the curing reaction under the water vapor atmosphere in Samples 3 to 8. The higher temperature condition than room temperature resulted in increasing the number of irregularities formed and thereby the number of pores formed. This is attributed to that the reaction of forming the irregularities (pores) on the top surface of a membrane by using the water vapor is a chemical reaction like the curing reaction and a temperature rise to a certain level ensures the more sufficient degree of activation.

In the case of using polyether for the polyol, at room temperature set to the curing temperature, irregularities were formed on the top surface, but no holes recognized as pores were observed (Sample 3). At 60° C. and at 80° C. set to the curing temperature, a large number of pores were observed on the top surface (Samples 4 and 5). Sample 4 employing the relatively lower curing temperature of 60° C., however, had the pores having the finer and more uniform pore diameter (refer to the image of the top surface at 1000-fold magnification) and had the greater membrane thickness. In the case of using polymer polyol for the polyol, on the other hand, at room temperature and at 60° C. set to the curing temperature, irregularities were formed on the top surface, but no holes recognized as pores were observed (Samples 6 and 7). At 80° C. set to the curing temperature, a large number of pores were observed on the top surface (Sample 8). By taking into account these results, it is contemplated that the aspect of irregularities or pores formed on the top surface of a membrane is adequately controlled by appropriately setting the curing conditions including the curing temperature according to the type of the polyurethane material used.

[Samples 9 to 11]

FIG. 12 is a chart showing the material compositions and the curing conditions of polyurethane membranes of Samples 9 to 11. The polyurethane membranes of Samples 9 and 10 were produced according to the production method shown in FIG. 4. The production method of the polyurethane membrane of Sample 11 differs by employing the dry atmosphere as the atmosphere at a step corresponding to step S120 as described later. The procedure of producing the polyurethane membranes of Samples 9 to 11 provided the materials of the compositions shown in FIG. 12 at step S100. As shown in FIG. 12, the types of the components included in the material used to produce the polyurethane membranes of Samples 9 to 11 and the film formation conditions are the same as those of Sample 1. FIG. 12 shows the compositions of the respective components in the same manner as FIG. 8.

The subsequent material layer formation step of S110 and curing step of step S120 were performed in the same manner as Sample 1. The curing temperature was, however, set to 50° C. for Sample 9 and was set to 60° C. for Samples 10 and 11.

Figure 13A:
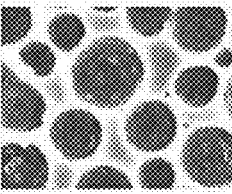
FIG. 13A is a chart showing the results of observation of the polyurethane membranes.
Figure 17:
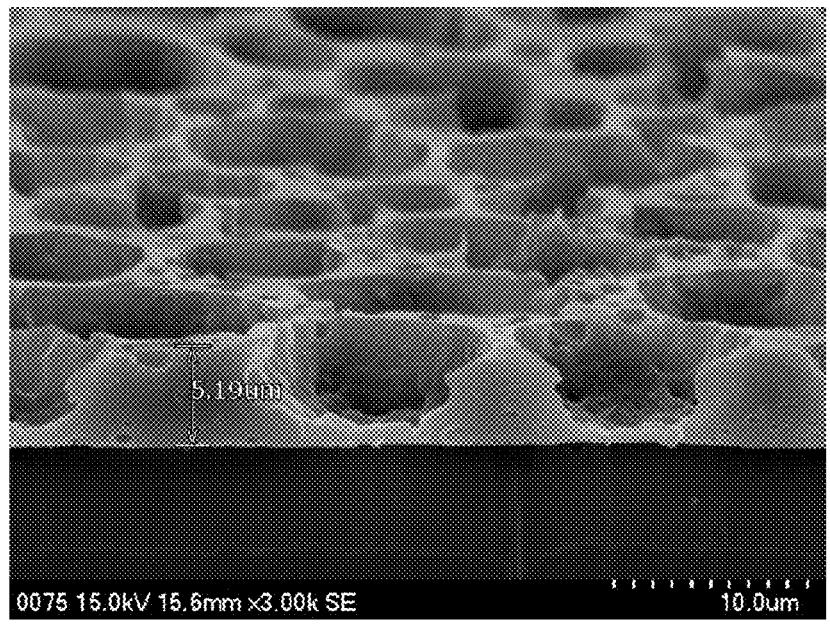
FIG. 17 is a photograph showing the result of observation of the polyurethane membrane.
Figure 18:
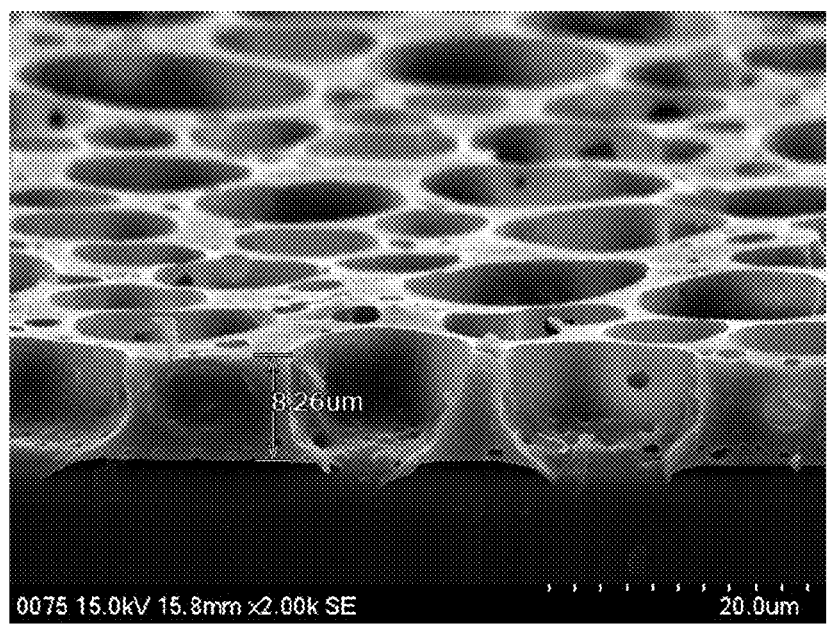
FIG. 18 is a photograph showing the result of observation of the polyurethane membrane.
Figure 19:
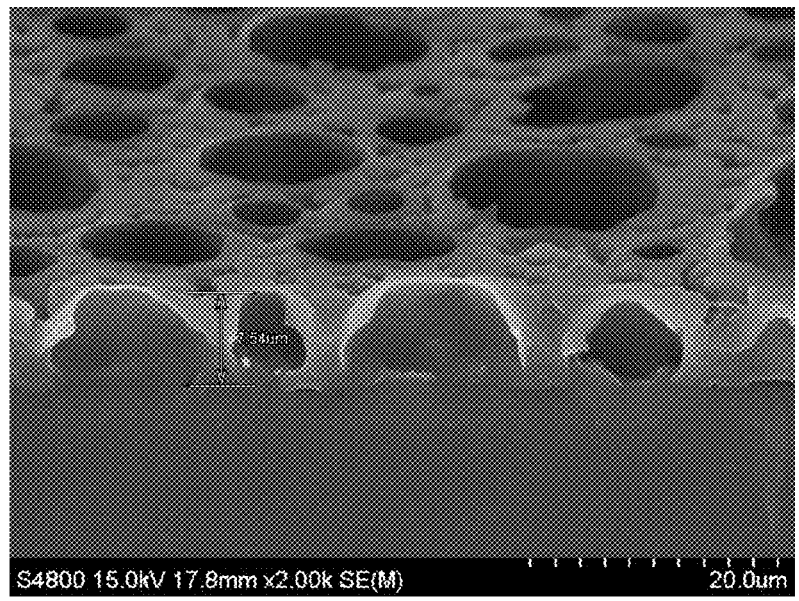
FIG. 19 is a photograph showing the result of observation of the polyurethane membrane.
Figure 20:
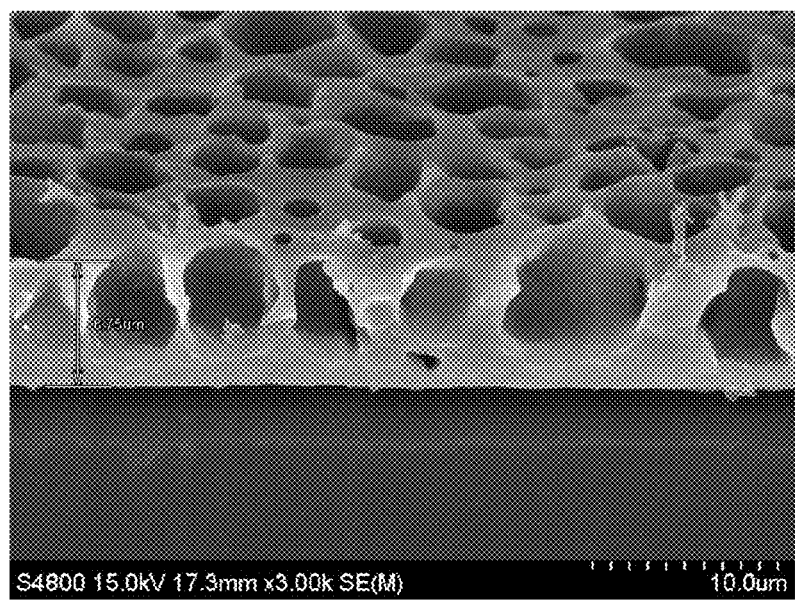
FIG. 20 is a photograph showing the result of observation of the polyurethane membrane.
Figure 21:
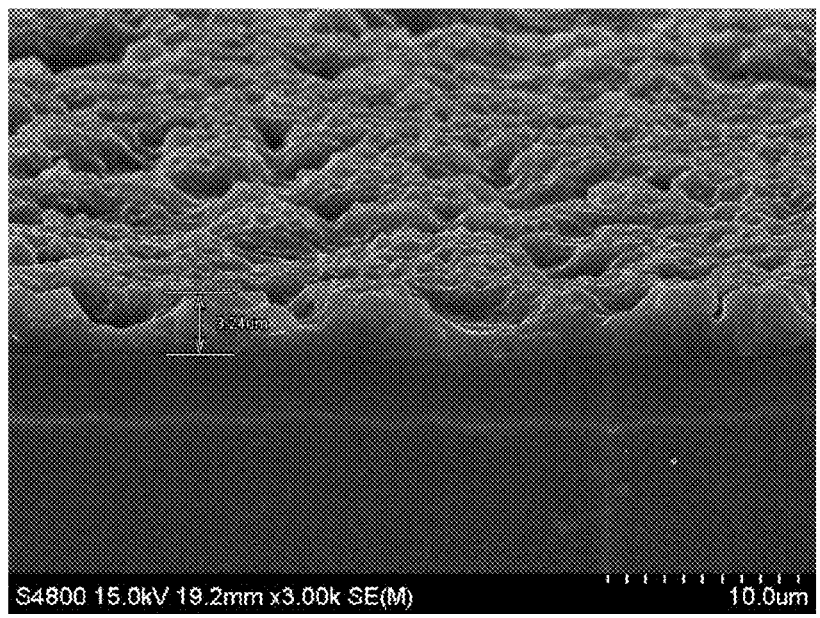
FIG. 21 is a photograph showing the result of observation of the polyurethane membrane.
Figure 22:
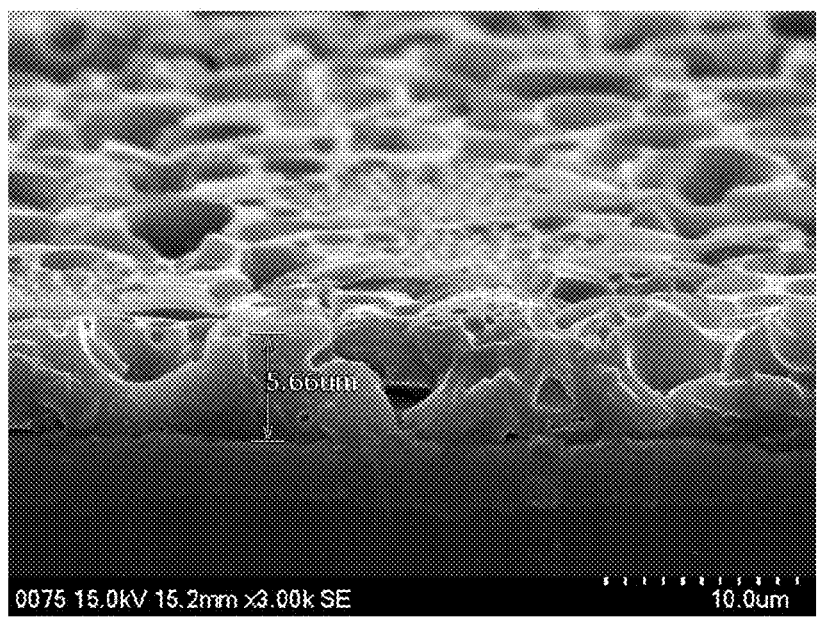
FIG. 22 is a photograph showing the result of observation of the polyurethane membrane.
Figure 23:
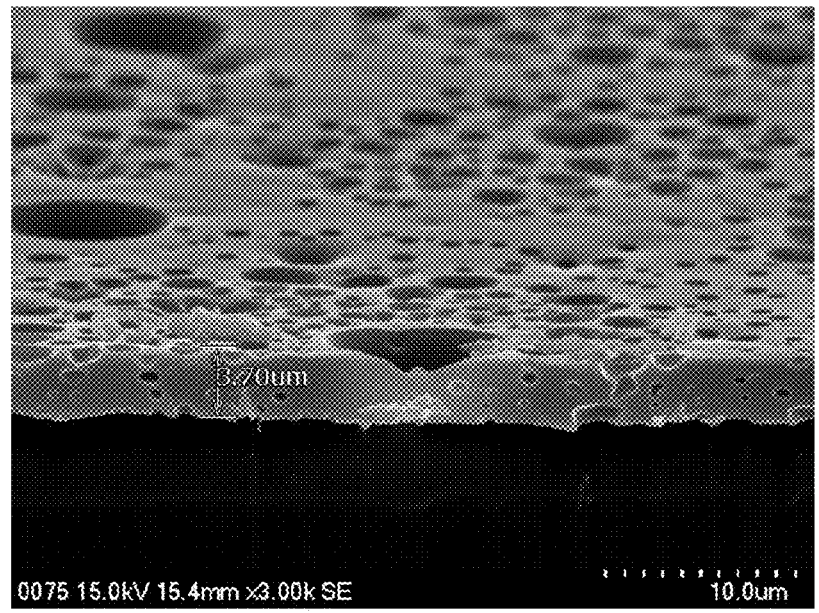
FIG. 23 is a photograph showing the result of observation of the polyurethane membrane.
Figure 24:
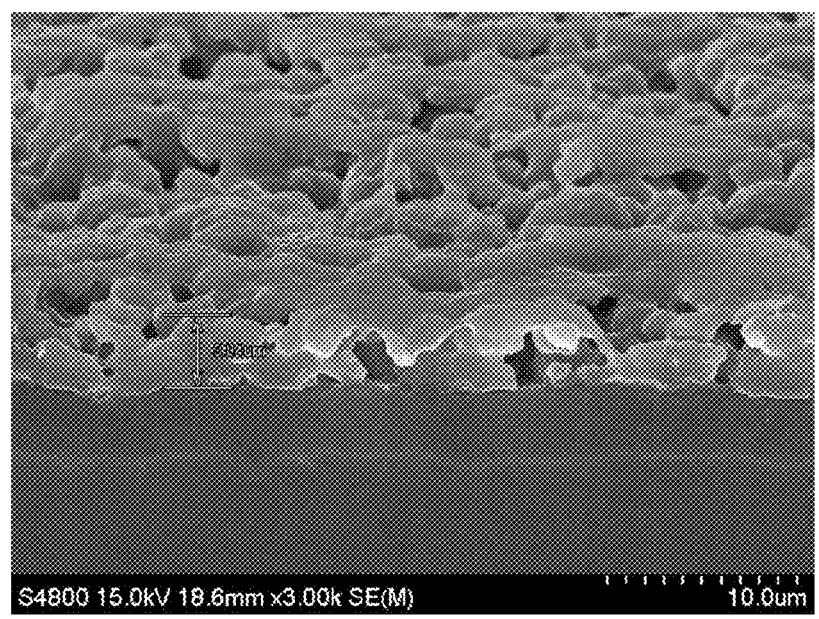
FIG. 24 is a photograph showing the result of observation of the polyurethane membrane.
Figure 25:
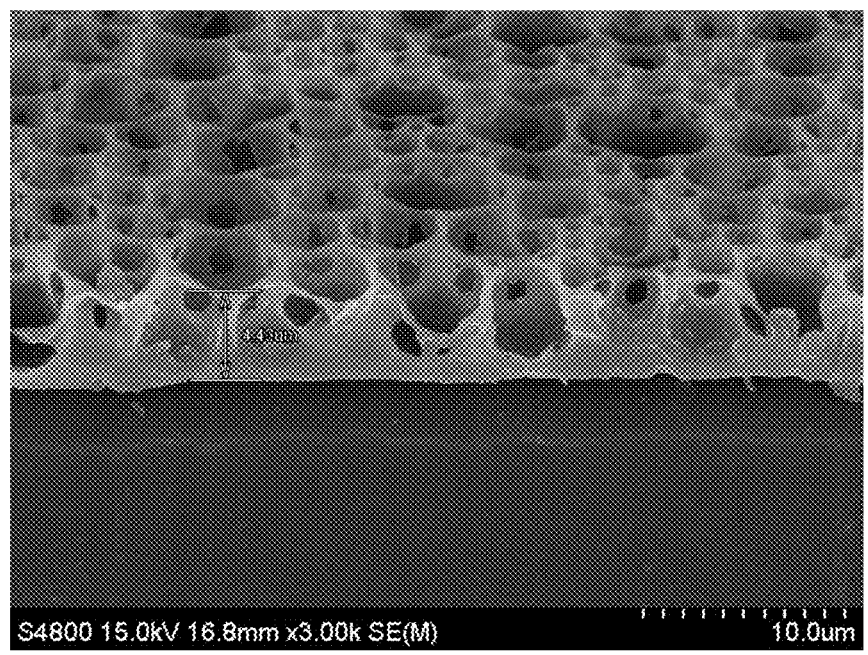
FIG. 25 is a photograph showing the result of observation of the polyurethane membrane.

FIGS. 13(A) and 13(B) are charts showing the results of observation of the polyurethane membranes of Samples 9 to 11 with the SEM in the same manner as Sample 1. As an example, FIG. 13(A) shows observation of the top surface, the bottom surface and the cross section of the polyurethane membrane at 3000-fold magnification. No formation of pores was observed with regard to Sample 11 as described below, so that observation of the bottom surface by removing the substrate was not performed for Sample 11. FIG. 13(B) shows the "membrane thickness at the crest" and the "membrane thickness at the trough" and their standard deviations, as well as the average pore diameters on the top surface and on the bottom surface and their standard deviations and the maximum value and the minimum value of the pore diameter with regard to each sample. An image of the top surface at 1000-fold magnification and an image of the bottom surface at 200-fold magnification were used for analysis of the pore diameters.

As shown in FIG. 13(A), pores passing through to the bottom surface were formed by the curing reaction under the water vapor atmosphere with respect to Samples 9 and 11. No formation of pores or irregularities was, however, observed in Sample 11 employing the curing reaction under the dry atmosphere.

According to comparison between Samples 9 and 10, Sample 10 employing the relatively higher curing temperature had the greater membrane thickness, although Samples 9 and 10 had the same material compositions. In other words, the material layers of Samples 9 and 10 formed at step S110 had substantially the same thicknesses, but Sample 10 had the greater membrane thickness after curing. This is attributed to that the foaming reaction using the water vapor proceeded more vigorously in Sample 10 employing the relatively higher curing temperature. According to comparison between Samples 9 and 10, Sample 9 employing the relatively lower curing temperature had the smaller pore diameter of the opening on the top surface of the pores and the smaller variation in pore diameter. Additionally, according to comparison of the pore diameter of the opening on the bottom surface, Sample 9 employing the relatively lower curing temperature had the greater average pore diameter but had the smaller variation in pore diameter. These results show that the chemical reaction involved in formation of pores proceeds more vigorously at the higher curing temperature and that a polyurethane porous membrane having pores passing through to the bottom surface and having the smaller pore diameter and the smaller variation in pore diameter is producible by adequately regulating the temperature of curing accompanied with the foaming reaction.

In Sample 4 and Sample 5 respectively employing the curing temperature of 60° C. and the curing temperature of 80° C. to perform curing under the water vapor atmosphere as described above, no pores passing through to the bottom surface were formed. In Sample 1 employing the curing temperature of 40° C., Sample 9 employing the curing temperature of 50° C. and Sample 10 employing the curing temperature of 60° C. to perform curing under the water vapor atmosphere, on the other hand, pores passing through to the bottom surface were formed. This is attributed to that Samples 1, 9 and 10 have the higher content ratios of the diluting solvent (amount of diluting solvent relative to 100 parts by mass of polyether) in the material than Samples 4 and 5 and thus reduce the thickness of the material layer subject to the curing reaction and are more likely to form through holes.

[Samples 12 to 14]

FIG. 14 is a chart showing the material compositions and the curing conditions of polyurethane membranes of Samples 12 to 14. The polyurethane membranes of Samples 12 and 13 were produced according to the production method shown in FIG. 7. The production method of the polyurethane membrane of Sample 14 differs by employing only one-step curing reaction under the dry atmosphere, in place of steps S120 and S130. The procedure of producing the polyurethane membranes of Samples 12 to 14 provided the materials of the compositions shown in FIG. 14 at step S100. As shown in FIG. 14, the types of the components included in the material used to produce the polyurethane membranes of Samples 12 to 14 and the film formation conditions are the same as those of Sample 1. FIG. 14 shows the compositions of the respective components in the same manner as FIG. 8.

With regard to Samples 12 and 13, the subsequent material layer formation step of S110 and curing step of step S120 were performed in the same manner as Sample 1. The differences from Sample 1 are that Sample 12 employed the curing reaction at the curing temperature of 40° C. for 30 minutes and Sample 13 employed the curing reaction at the curing temperature of 50° C. for 30 minutes at step S120. In Samples 12 and 13, curing was accelerated under the dry atmosphere at subsequent step S130. More specifically, the procedure removed liquid water from the airtight container to change the atmosphere from the water vapor atmosphere to the dry atmosphere and continued the curing reaction at 60° C. overnight. In Sample 14, on the other hand, the procedure performed the curing reaction under the dry atmosphere at the curing temperature of 60° C. overnight without performing the curing reaction under the water vapor atmosphere at step S120.

FIGS. 15(A) and 15(B) are charts showing the results of observation of the polyurethane membranes of Samples 12 to 14 with the SEM in the same manner as Sample 1. As an example, FIG. 15(A) shows observation of the top surface of each polyurethane membrane at 500-fold magnification and the cross section at 1000-fold magnification. FIG. 15(A) also shows observation of the bottom surface at 200-fold magnification for Sample 12 and observation of the bottom surface at 500-fold magnification for Sample 13. No formation of pores was observed with regard to Sample 14 as described below, so that observation of the bottom surface by removing the substrate was not performed for Sample 14. FIG. 15(B) shows the "membrane thickness at the crest" and the "membrane thickness at the trough" and their standard deviations, as well as the average pore diameters on the top surface and on the bottom surface and their standard deviations and the maximum value and the minimum value of the pore diameter with regard to each sample. An image of the top surface at 500-fold magnification and an image of the bottom surface at 200-fold magnification were used for analysis of the pore diameters.

As shown in FIG. 15(A), in Samples 12 and 13 performing the curing reaction under the water vapor atmosphere, formation of pores passing through to the bottom surface was observed. In Sample 14 performing the curing reaction only under the dry atmosphere, on the other hand, no formation of pores or irregularities was observed.

According to comparison between Samples 12 and 13, Sample 13 employing the relatively higher curing temperature had the greater membrane thickness, although Samples 12 and 13 had the same material compositions (although the material layers of Samples 12 and 13 had substantially the same thicknesses). This is attributed to that the foaming reaction using the water vapor proceeded more vigorously in Sample 13 employing the relatively higher curing temperature. According to comparison between Samples 12 and 13, Sample 12 employing the relatively lower curing temperature under the water vapor atmosphere had the smaller pore diameters (average pore diameter, maximum value and minimum value) of pores and the smaller variations in pore diameter (standard deviations of pore diameter) on both the top surface and the bottom surface.

An interference pattern was observed on the top surface of the polyurethane porous membrane in Sample 12 employing the reaction temperature of 40° C. at step S120 as the first step of the curing reaction. The presence of this interference pattern indicates a very small variation in pore diameter of the plurality of pores open to the top surface of the membrane. Even at the temperature of curing accompanied with the foaming reaction set to 40° C., however, when step S130 of accelerating curing under the dry atmosphere was not performed like Sample 1 described above, no interference pattern was observed on the top surface of the polyurethane porous membrane in any sample (such data of interference pattern are not shown). These results show that the smaller average pore diameter and the smaller variation in pore diameter are obtainable by setting the shorter time for the curing reaction accompanied with the foaming reaction using the water vapor and subsequently accelerating the curing reaction under the dry atmosphere. This is attributed to that the two-step curing reaction employing the water vapor atmosphere only for the first step stops the foaming reaction in the state of the small and uniform pore diameter, prior to the excessive progress of the foaming reaction.

[Samples 15 to 23]

FIGS. 16(A) and 16(B) are charts showing the material compositions and the curing conditions of polyurethane membranes of Samples 15 to 23 and the measurement results of the surfaces of the resulting polyurethane porous membranes. The polyurethane membranes of Samples 15 to 23 were produced according to the production method shown in FIG. 7. FIGS. 16(A) and 16(B) show the compositions of the respective components in the materials as the mass ratios of the respective components relative to 100 parts by mass of polyol.

As shown in FIGS. 16(A) and 16(B), Samples 15 to 23 used different types of polyol and isocyanate for the material of the polyurethane membrane from those of Samples 1 to 14 described above. The following polyols were used in the respective Samples. The polyol used in Sample 15 was polyether polyol having hydroxyl value of 397 (polyoxypropylene glyceryl ether). The polyol used in Sample 16 was polymer polyol having hydroxyl value of 27 (obtained by radical polymerization of styrene and acrylonitrile in polyether polyol of addition polymerization of propylene oxide and ethylene oxide to glycerol). The polyol used in Sample 17 was polyester polyol having hydroxyl value of 56 (poly(ethylene adipate) diol). The polyol used in Sample 18 was polycarbonate diol having hydroxyl value of 55.

The isocyanate used in Sample 19 was monomeric MDI containing 33.6% by mass of isocyanate group (NCO) at the molecular end. The isocyanate used in Sample 20 was polyol-modified MDI containing 23.1% by mass of isocyanate group (NCO) at the molecular end. The isocyanate used in Sample 21 was polymeric MDI containing 30.7% by mass of isocyanate group (NCO) at the molecular end. The isocyanate used in Sample 22 was carbodiimide-modified MDI containing 28.7% by mass of isocyanate group (NCO) at the molecular end. The crosslinking agent used in Sample 23 was ethylene glycol. The other components used in Samples 15 to 23 were the same as those used in Samples 1 to 14. FIGS. 16(A) and 16(B) show the compositions of the materials of the polyurethane membranes by the amounts relative to 100 parts by mass of polyol. The conditions of steps S110 to S130 employed in production of Samples 15 to 23 were identical with those employed in Sample 12 described above.

FIGS. 17 to 25 show observation of the respective produced polyurethane membranes of Samples 15 to 23 from an angle at 2000-fold magnification or at 3000-fold magnification with a scanning electron microscope (SEM, S-800 manufactured by Hitachi, Ltd.) at the accelerating voltage of 15 kV. As shown in FIGS. 17 to 25, it is confirmed that polyurethane porous membranes having a plurality of pores open to at least the top surface 22 are producible by using different types of the polyol, the isocyanate or the crosslinking agent. FIGS. 16(A) and 16(B) also show the membrane thicknesses of the respective polyurethane porous membranes of Samples 15 to 23 and the average pore diameters on the top surface 22 (size of top surface pore).

<Cell Culture Using Polyurethane Porous Membrane>

The following describes the results of cell culture using polyurethane porous membranes prepared as described below (Samples 24 and 25).

[Samples 24 and 25]

FIG. 26 is a chart showing the material compositions and the curing conditions of polyurethane porous membranes of Samples 24 and 25 and the measurement results of the surfaces of the resulting polyurethane porous membranes. The polyurethane porous membranes of Samples 24 and 25 were produced according to the production method shown in FIG. 7. The types of the components of the materials used in production of the polyurethane porous membranes of Samples 24 and 25 were the same as those used in Sample 1. FIG. 26 shows the compositions of the respective components in the same manner as FIG. 8.

The conditions of steps S110 to S130 employed in production of Samples 24 and 25 were identical with those employed in Sample 12 described above. Samples 24 and 25 employed different times between mixing of the materials at step S100 (mixing step) and spin coating at step S110 (layer formation step). Sample 24 was left to stand at room temperature for 12 minutes between the mixing step and the layer formation step, and Sample 25 was left to stand at room temperature for 30 minutes between the mixing step and the layer formation step.

Sample 24 prepared as described above was a through-hole membrane having pores passing through to the bottom surface 24. Sample 25 was a non-through-hole membrane. The "non-through-hole" membrane herein means that the total area of pores in a specific visual field of the bottom surface 24 of the membrane (surface adjacent to the substrate during production) observed at 2000-fold magnification is less than 5% of the entire area of the visual field. The area of the pores on the bottom surface 24 is determined by image analysis using image analysis software Mac-View (manufacture by Mountech Co., Ltd.), like the "size of top surface pore" described above.

In the polyurethane porous membrane of Sample 24, the average pore diameter on the top surface 22 (size of top surface pore) was 14 μm; the average pore diameter on the bottom surface 24 (size of bottom surface pore) was 11 μm; and the membrane thickness (membrane thickness at the crest) was 6 μm. In Sample 25, the average pore diameter on the top surface 22 was 3 μm, and the membrane thickness was 3 μm. As described above, Sample 24 employing the shorter time between the mixing step and the layer formation step provided a through-hole membrane, whereas Sample 25 employing the longer time between the mixing step and the layer formation step provided a non-through-hole membrane having the smaller average pore diameter on the top surface 22.

[Cell Culture Conditions]
(i) Cell Line

Figure 27:
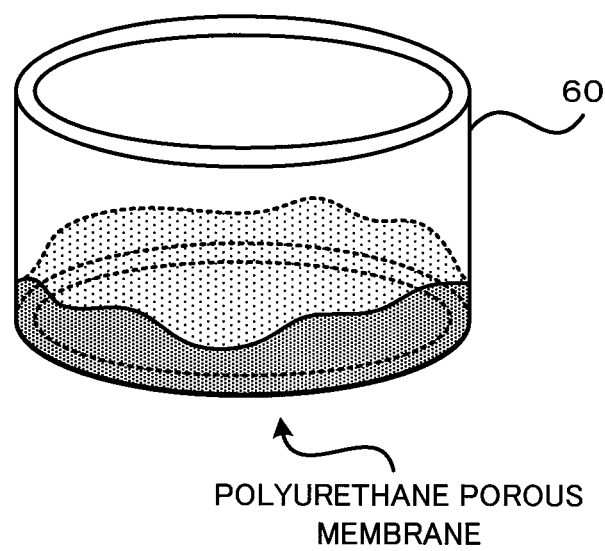
FIG. 27 is a perspective view schematically illustrating a cell culture device.

The following two cell lines were used for culture:

HUVEC (human umbilical vein endothelial cell): HUVEC-C (National Institute of Biomedical Innovation, JCRB Cell Bank, IFO50271); and AoSMC (human aortic smooth muscle cell): AoSMC (Lonza, CC-2571).
(ii) Culture Medium The culture medium for HUVEC was DMEM-12 (Gibco, 11330-057) with addition of penicillin streptomycin (Gibco, 15140-122), heparin sodium salt (SIGMA-ALDRICH, H3149-100KU) and ECGS (endothelial cell growth supplement) (SIGMA, E2759). The culture medium for AoSMC was SmGM-2 (trademark) Smooth Muscle Cell Medium BulletKit (trademark) (Lonza, CC-3182).
(iii) Cell Culture Device FIG. 27 is a perspective view schematically illustrating a cell culture device 60 used in cell culture using both surfaces of a polyurethane porous membrane. The cell culture device 60 is a ring-shaped member which is made of glass and has the outer diameter of 13 mm.

Figure 28:
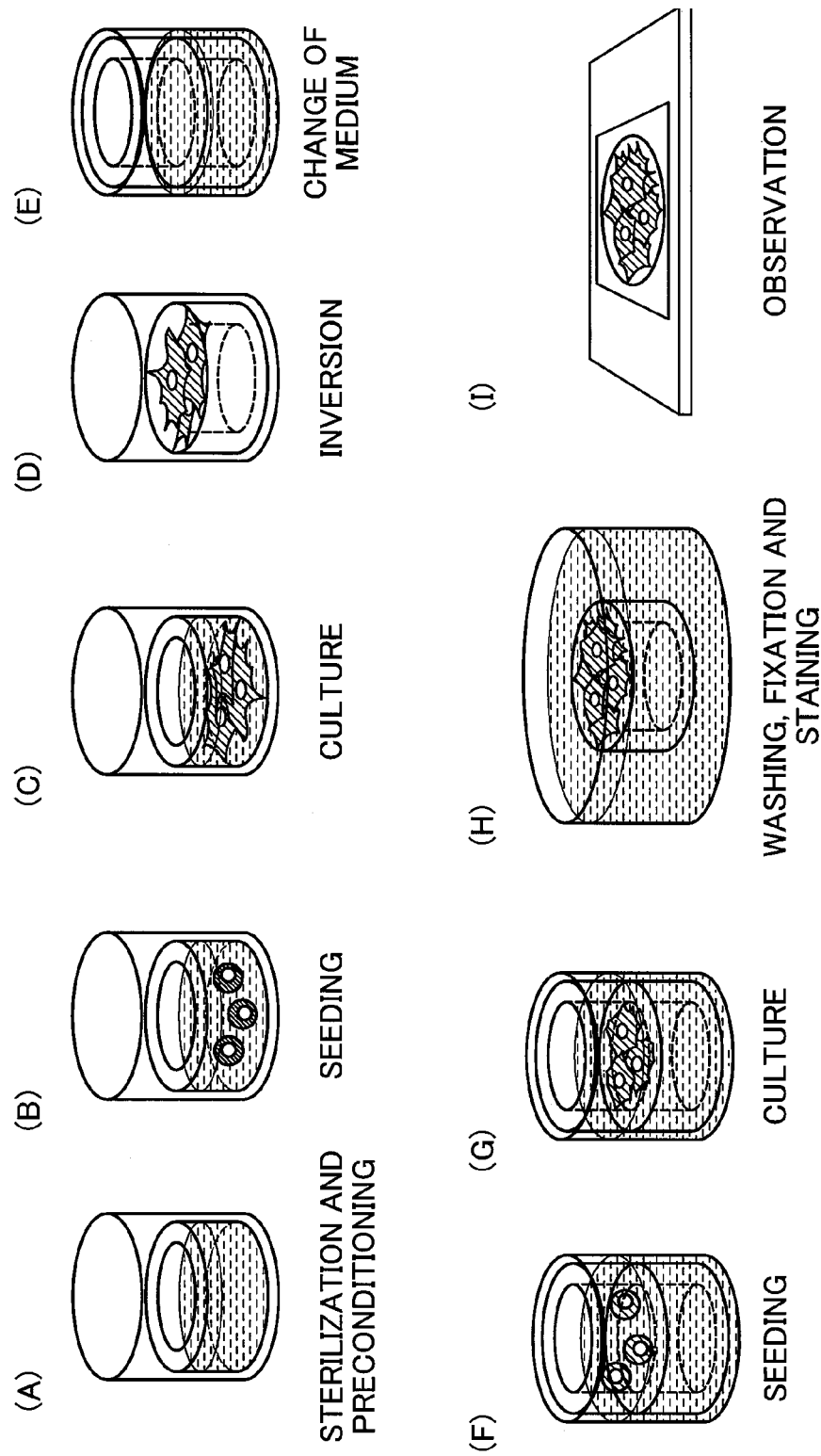
FIG. 28 is a diagram illustrating a cell culture process on both surfaces of a polyurethane porous membrane.

In the process of cell culture, the polyurethane porous membrane was placed to cover one opening of the above ring-shaped cell culture device 60. More specifically, the process attached in advance a double-sided adhesive tape at two different positions on the side face of the cell culture device 60, mounted the polyurethane porous membrane on the cell culture device 60 in ethanol, and bonded the periphery of the polyurethane porous membrane to the double-sided adhesive tape. The process subsequently removed ethanol and dried the polyurethane porous membrane, so as to fix the polyurethane porous membrane to the cell culture device 60. In the case of double (top and bottom)-sided culture described below or in the case of single-sided culture with cell seeding on the top surface 22, the polyurethane porous membrane was placed such that the top surface 22 of the polyurethane porous membrane was exposed inside of the ring-shaped cell culture device 60. In the case of single-sided culture with cell seeding on the bottom surface 24, on the other hand, the polyurethane porous membrane was placed such that the bottom surface 24 of the polyurethane porous membrane was exposed inside of the ring-shaped cell culture device 60.
(iv) Cell Culture Process
(iv)-1. Double (Top and Bottom)-Sided Culture FIG. 28 is a diagram illustrating a cell culture process on both surfaces of the polyurethane porous membrane using the cell culture device 60. The cell culture process first preconditioned the polyurethane porous membrane attached to the cell culture device 60 overnight in the medium for AoSMC after UV sterilization (FIG. 28(A)). The process subsequently seeded AoSMC on the top surface 22 of the polyurethane porous membrane (FIG. 28(B)) and cultured AoSMC for five days under the conditions of 37° C. and 5% $CO_2$ (FIG. 28(C)). The process then vertically inverted the cell culture device 60 (FIG. 28(D)) and exchanged the medium to the medium for HUVEC (FIG. 28(E)). The process subsequently seeded HUVEC on the bottom surface 24 of the polyurethane porous membrane (FIG. 28(F)) and cultured HUVEC for three days under the conditions of 37° C. and 5% $CO_2$ (FIG. 28(G)).
(iv)-2. Single (Top or Bottom)-Sided Culture In the case of single (top or bottom)-sided culture, cells were seeded only one of the surfaces of the polyurethane porous membrane attached to the cell culture device 60 (surface exposed inside of the ring-shaped cell culture device 60). In the case of single-sided culture, the process preconditioned the polyurethane porous membrane attached to the cell culture device 60 overnight in the medium for the cells to be seeded after UV sterilization. The process subsequently seeded HUVEC or AoSMC on the top surface 22 or on the bottom surface 24 of the polyurethane porous membrane and cultured HUVEC for three days or AoSMC for four days under the conditions of 37° C. and 5% $CO_2$.

[Evaluation Method]

After the cell culture, the polyurethane porous membrane attached to the cell culture device 60 was washed once with PBS (phosphate buffered saline). The process subsequently treated with a 4% para-formaldehyde/phosphate buffer solution for tissue fixation (163-20145, manufactured by Wako Pure Chemical Industries, Ltd.) under the environment of 37° C. for ten minutes to fix the cells and treated with a 1% Triton-X100-containing PBS and a 0.02% Tween 20-containing PBS to provide the cell membrane with permeability. The respective cells were then observed as described below.

For HUVEC, a mouse antibody (SIGMA, P8590) to CD31 as the cell surface receptor which is intensively expressed on the surface of endothelial cells was used as the primary antibody, and an anti-mouse IgG antibody (Invitrogen, A-11004) was used as the secondary antibody. Excitation of a fluorescent material in the cells treated with the secondary antibody caused CD31 of HUVEC to be stained red.

For AoSMC, a rabbit antibody (abcam, ab32575) to αSMA which is a cell skeletal protein of smooth muscle cell was used as the primary antibody, and an anti-rabbit IgG antibody (Invitrogen, A-11008) was used as the secondary antibody. Excitation of a fluorescent material in the cells treated with the secondary antibody caused αSMA of AoSMC to be stained green (from washing to staining, FIG. 28(H)).

After the above treatment, the polyurethane porous membrane was detached from the cell culture device 60 and was sealed on a glass slide. The cell-cultured surface of the polyurethane porous membrane was observed with a laser confocal microscope (FIG. 28(I)).

[Results of Cell Culture]

Figure 29:
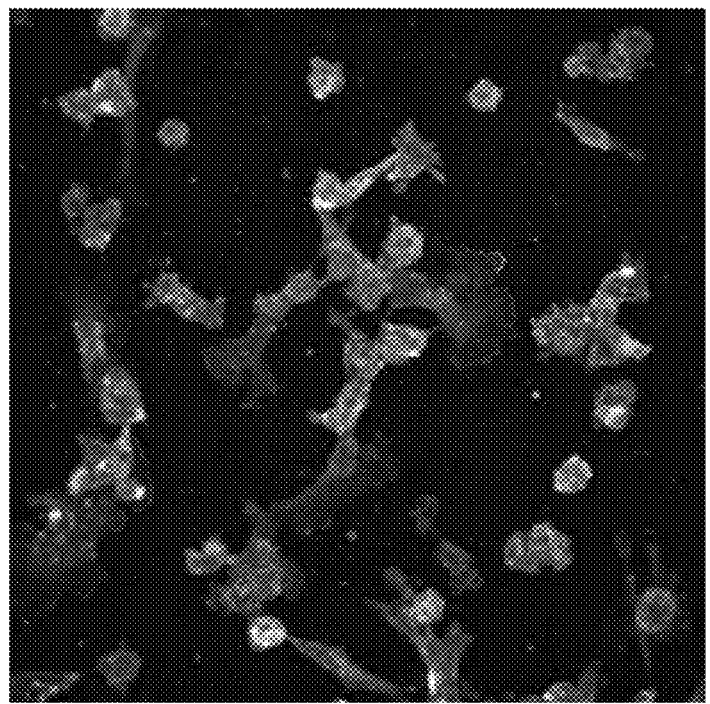
FIG. 29 is a photograph showing the result of single-sided culture with HUVEC seeded on a top surface.
Figure 30:
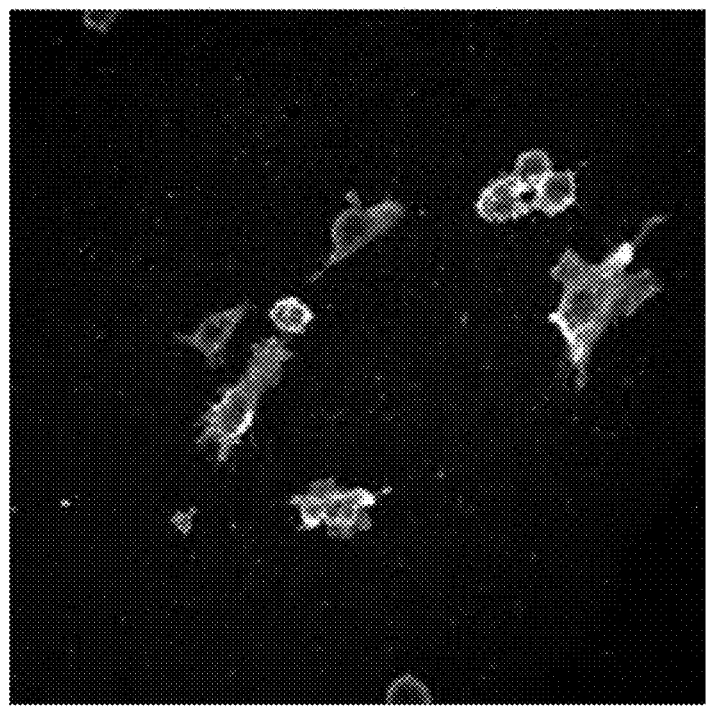
FIG. 30 is a photograph showing the result of single-sided culture with HUVEC seeded on a top surface.

FIG. 29 is a photograph showing the result of single-sided culture with HUVEC seeded on the top surface 22 of the polyurethane porous membrane of Sample 25 (non-through-hole membrane). FIG. 30 is a photograph showing the result of single-sided culture with HUVEC seeded on the bottom surface 24 of the polyurethane porous membrane of Sample 25 (non-through-hole membrane). In both cases, the seeding density of HUVEC was $5.0 \times 10^4$ cells/cm$^2$. FIG. 29 and FIG. 30 are both the results of observation at 400-fold magnification.

According to comparison between FIG. 29 and FIG. 30, the better cell growth was observed on the top surface 22 of the polyurethane porous membrane (non-through-hole membrane) than the bottom surface 24. This result proves that the polyurethane porous membrane made porous (to form irregularities) with the supply of water vapor during curing of polyurethane serves as the better cell culture membrane than a polyurethane membrane without such irregularities.

Figure 31A:
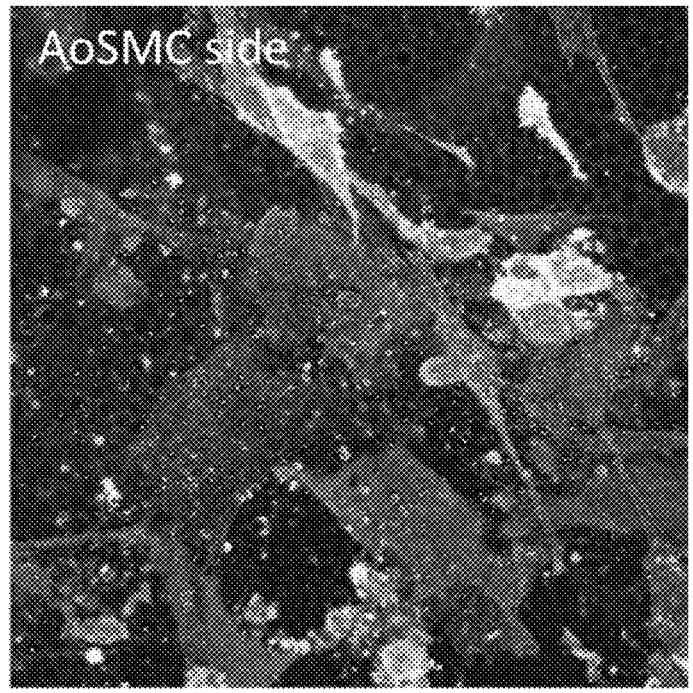
FIGS. 31A and 31B are photographs showing the results of double (top and bottom)-sided culture with AoSMC seeded on the top surface and HUVEC seeded on the bottom surface.
Figure 31B:
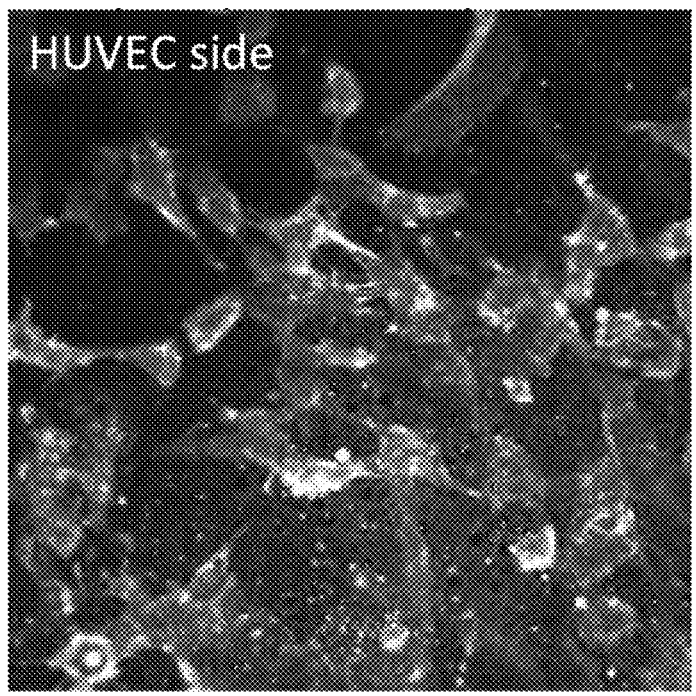
Figure 32A:
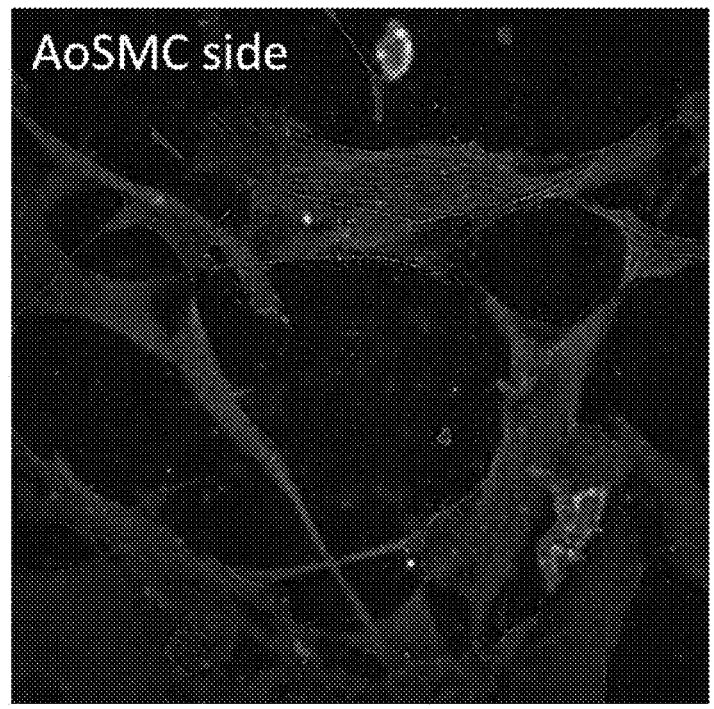
FIGS. 32A and 32B are photographs showing the results of double (top and bottom)-sided culture with AoSMC seeded on the top surface and HUVEC seeded on the bottom surface.
Figure 32B:
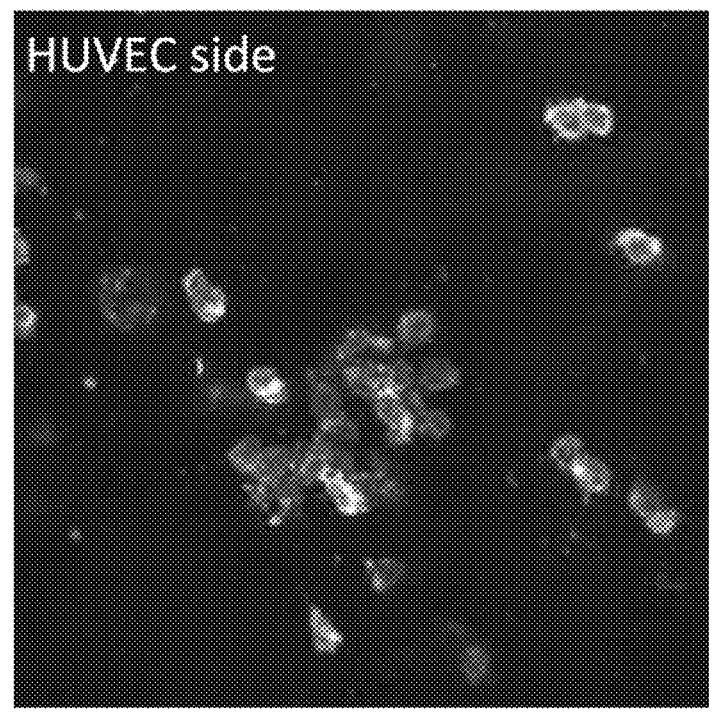

FIGS. 31A and 31B are photographs showing the results of double (top and bottom)-sided culture with AoSMC seeded on the top surface 22 and HUVEC seeded on the bottom surface 24 of the polyurethane porous membrane of Sample 24 (through-hole membrane). FIGS. 32A and 32B are photographs showing the results of double (top and bottom)-sided culture with AoSMC seed on the top surface 22 and HUVEC seeded on the bottom surface 24 of the polyurethane porous membrane of Sample 25 (non-through-hole membrane). In both cases, the seeding density of AoSMC was $1.0 \times 10^4$ cells/cm$^2$ and the seeding density of HUVEC was $5.0 \times 10^4$ cells/cm$^2$. FIGS. 31A and 31B and FIGS. 32A and 32B are all the results of observation at 400-fold magnification.

According to comparison between FIGS. 31A and 31B and FIGS. 32A and 32B, the polyurethane porous membrane of Sample 24 (through-hole membrane) provided the better cell growth of both AoSMC and HUVEC than the polyurethane porous membrane of Sample 25 (non-through-hole membrane). This may be attributed to the effect of interaction between AoSMC and HUVEC via the pores of the polyurethane membrane. Accordingly, it is contemplated that interaction between different cells can be analyzed by cell culture on both surfaces of the polyurethane porous membrane having through holes, such as Sample 24.

<Cancer Cell Growth Inhibition by Polyurethane Porous Membrane>

The following describes the study results of the cancer cell growth inhibition effect using polyurethane porous membranes prepared as described below (Samples 26, 27 and 28).

[Samples 26 to 28]

FIG. 33 is a chart showing the material compositions and the curing conditions of polyurethane membranes of Samples 26 to 28 and the measurement results of the surfaces of the resulting polyurethane membranes. The polyurethane porous membranes of Samples 26 and 27 were produced according to the production method shown in FIG. 7. The polyurethane membrane of Sample 28 was produced without curing with the supply of water vapor at step S120 as described below. As shown in FIG. 33, the types of the components of the materials used in production of the polyurethane membranes of Samples 26 to 28 were the same as those used in Sample 1. FIG. 33 shows the compositions of the respective components in the same manner as FIG. 8.

Samples 26 and 27 performed the layer formation step of step S110 in the same manner as Sample 1, subsequently performed the curing reaction under the water vapor atmosphere at 40° C. for 30 minutes at step S120 and performed the curing reaction under the dry atmosphere at 60° C. overnight at step S130. Sample 28 performed spin coating at the rotation speed of 2000 rpm for 60 seconds at room temperature in the layer formation step of step S110 and subsequently performed the curing reaction under the dry atmosphere at 60° C. overnight without performing the curing reaction under the water vapor atmosphere.

Samples 26 and 27 prepared as described above were non-through-hole membranes having pores not passing through to the bottom surface 24. Sample 28 was a non-porous membrane substantially with no formation of pores. The "non-porous membrane" herein means that the total area of pores in a specific visual field of the top surface 22 of the membrane (surface away from the substrate during production) observed at 2000-fold magnification is less than 5% of the entire area of the visual field. As shown in FIG. 33, in the polyurethane porous membrane of Sample 26, the average pore diameter on the top surface (size of top surface pore) was 16.2 μm, and the membrane thickness (membrane thickness at the crest) was 9 μm. In sample 27, the average pore diameter on the top surface was 11.1 μm, and the membrane thickness was 14 μm. In Sample 28, the membrane thickness was 6 μm.

[Cell Culture Conditions]

(i) Cell Line

The following two cell lines were used for culture:
TOV21G (human ovary cancer cell): CRL-11730 (ATCC, American Type Culture Collection); and
Caov3 (human ovary cancer cell): HTB-75 (ATCC)

(ii) Culture Medium

The culture medium for TOV21G was prepared by mixing 45 mL of a 1:1 mixed medium of M199 medium (Sigma, M4530) and M105 medium (Sigma, M6395) with 5 mL of FBS (Hyclone, SH30071.03) and further adding 500 μL of penicillin (Thermo scientific, SV30010). The culture medium for Caov3 was prepared by adding 500 μL of penicillin (Thermo scientific, SV30010) and 1 mL of L-glutamic acid solution (Sigma, G7513) to a mixed medium of 45 mL of DMEM medium (Sigma, D5921) and 5 mL of FBS (Hyclone, SH30071.03).

(iii) Cell Culture Process

TOV21G was seeded and cultured respectively on Sample 26 (polyurethane porous membrane), Sample 28 (polyurethane smooth membrane) and a cell culture plate (HTB-75, Falcon). Caov3 was seeded and cultured respectively on Sample 27 (polyurethane porous membrane), Sample 28 (polyurethane smooth membrane) and a cell culture plate (HTB-75, Falcon). When the cells were seeded on Samples 26 to 28, the polyurethane membrane formed on the substrate was used without being detached from the substrate.

The cell culture process first preconditioned the polyurethane membrane formed on the substrate overnight in the medium for the cells to be seeded, after UV sterilization. The process subsequently seeded TOV21G or Caov3. The seeding density was $1.0 \times 10^4$ cells/cm$^2$ for both the cells. The respective seeded cells were cultured for 48 hours under the conditions of 37° C. and 5% $CO_2$.

[Evaluation Method]

The number of cells (cell density) after culture was measured, and the cell growth rate was determined with respect to each polyurethane membrane. More specifically, the cell growth rate was determined as the number of cells (cell density) on the polyurethane membrane after culture relative to the number of cells (cell density) on the cell culture plate after culture set to 100. This cell density was calculated as an average value of cell densities measured in five visual fields selected at random in observation of the cell culture plate or each of the polyurethane membranes at 100-fold magnification using a fluorescence microscope (manufactured by OLYMPUS CORPORATION). The lower cell growth rate indicates the higher degree of cell growth inhibition.

[Results of Evaluation]

Figure 34:
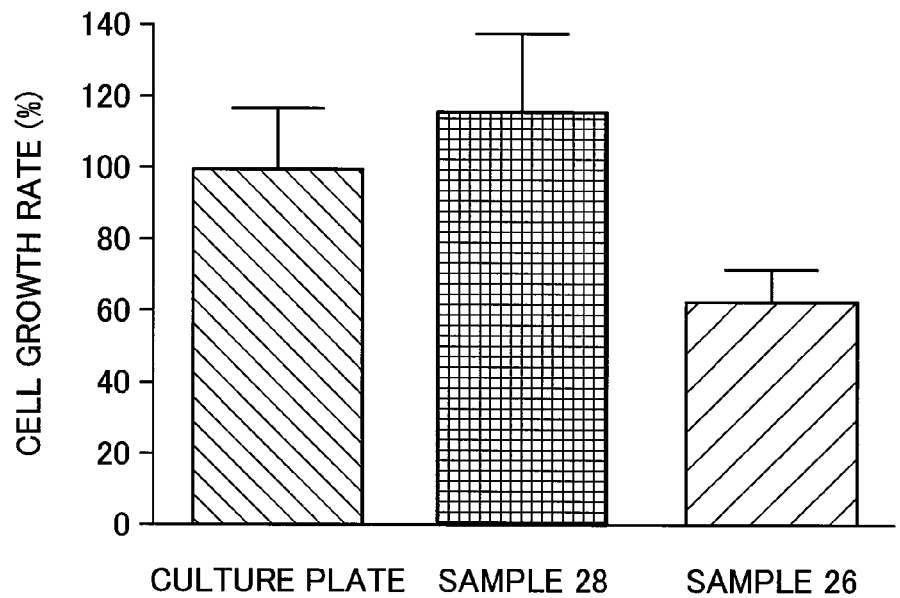
FIG. 34 is a bar graph showing cell growth rates by culture of TOV21G.
Figure 35:
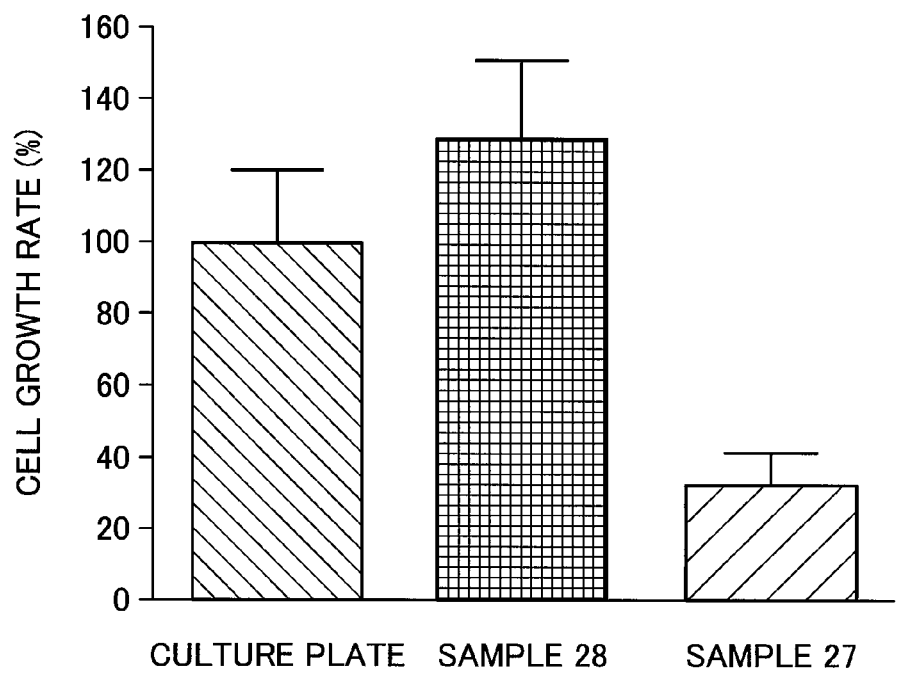
FIG. 35 is a bar chart showing cell growth rates by culture of Caov3.

FIG. 34 is a bar graph showing the results of culture of TOV21G seeded respectively on Sample 26, Sample 28 and the culture plate. FIG. 35 is a bar graph showing the results of culture of Caov3 seeded respectively on Sample 27, Sample 28 and the culture plate. Standard deviations are also shown in the bar graphs of FIGS. 34 and 35.

As shown in FIGS. 34 and 35, in either of the cancer cells, the polyurethane smooth membrane (Sample 28) had the higher cell growth rate, compared with the culture plate. The polyurethane porous membranes (Sample 26 and Sample 27), on the other hand, had the lower cell growth rates, compared with the culture plate. This proves the effects of cancer cell growth inhibition.

The invention is not limited to the above embodiments, examples or modifications, but a diversity of variations and modifications may be made to the embodiments without departing from the scope of the invention. For example, the technical features of the embodiments, examples or modifications corresponding to the technical features of the respective aspects described in Summary may be replaced or combined appropriately, in order to solve part or all of the problems described above or in order to achieve part or all of the advantageous effects described above. Any of the technical features may be omitted appropriately unless the technical feature is described as essential herein.

The invention claimed is:

1. A production method of a polyurethane porous membrane to be used for at least one of applications of cell culture and cancer cell growth inhibition, the production method of the polyurethane porous membrane comprising:
   a first step of forming a layer of uncured polyurethane material on a substrate, the layer of uncured polyurethane material having a first surface adjacent the substrate and an exposed surface opposite the first surface; and
   a second step of supplying water vapor and contacting the exposed surface of the layer of uncured polyurethane material formed on the substrate with an effective amount of the water vapor effective to cure the uncured polyurethane material and to convert the uncured polyurethane material into a polyurethane porous membrane with a porous structure having a thickness of 0.1 to 100 µm and including a plurality of pores open to the exposed surface having an average pore diameter of 0.1 to 100 µm, the plurality of pores open to the exposed surface forming a plurality of irregularities on the exposed surface, wherein
   the porous structure of the polyurethane porous membrane only contains a single pore extending along a membrane thickness direction of the polyurethane porous membrane.

2. The production method of the polyurethane porous membrane to be used for at least one of the applications of cell culture and cancer cell growth inhibition according to claim 1,
   wherein the second step includes a reaction temperature and a reaction time effective for forming the polyurethane porous membrane having the thickness of 0.1 to 100 µm.

3. The production method of the polyurethane porous membrane to be used for at least one of the applications of cell culture and cancer cell growth inhibition according to claim 1,
   wherein the second step includes a reaction time effective for forming the polyurethane porous membrane having the thickness of 0.1 to 100 µm.

4. The production method of the polyurethane porous membrane to be used for at least one of the applications of cell culture and cancer cell growth inhibition according to claim 1,
   wherein the plurality of pores open to the exposed surface of the polyurethane porous membrane include pores passing through to the first surface of the layer of polyurethane material adjacent to the substrate.

5. The production method of the polyurethane porous membrane to be used for at least one of the applications of cell culture and cancer cell growth inhibition according to claim 4,
   wherein the second step includes a reaction temperature and a reaction time effective for forming the pores open to the exposed surface of the polyurethane porous membrane and passing through polyurethane porous membrane.

6. The production method of the polyurethane porous membrane to be used for at least one of the applications of cell culture and cancer cell growth inhibition according to claim 4,
   wherein the first step comprises substeps of:
      a mixing step of mixing the polyurethane material including at east a polyol and an isocyanate; and
      a layer formation step of forming the polyurethane material mixed in the mixing step to the layer, and
   wherein an amount of time between the mixing step and the layer formation step and an environment temperature of the polyurethane material between the mixing step and the layer formation step are effective for forming the pores passing through to the first surface of the layer of the polyurethane material adjacent to the substrate.

7. The production method of the polyurethane porous membrane to be used for at least one of the applications of cell culture and cancer cell growth inhibition according to claim 1, the production method of the polyurethane porous membrane further comprising:
   an additional step of curing the polyurethane material without supplying the water vapor, after the second step.

8. The production method of the polyurethane porous membrane according to claim 1,
   wherein the substrate is a film made of a material selected from polypropylene, fluororesin, polyethylene terephthalate, polyethylene, polyvinylidene chloride, polyamide and polyimide.

9. The production method of the polyurethane porous membrane according to claim 1, the production method of the polyurethane porous membrane further comprising:
   a fourth step of removing the substrate from the polyurethane porous membrane, after the second step.

10. The production method of the polyurethane porous membrane according to claim 1, wherein each of the pores open to the exposed surface of the polyurethane porous membrane has a curved inner wall surface that is convex toward the first surface.

11. The production method of the polyurethane porous membrane according to claim 1, wherein
the irregularities on the exposed surface of the polyurethane porous membrane have widths of not greater than 20% of the membrane thickness.

12. The production method of the polyurethane porous membrane according to claim 1, wherein
the second step is carried out in an airtight container, the layer of uncured polyurethane material is arranged in the container with the exposed surface facing downward and the water vapor is supplied from below the layer of uncured polyurethane material.

* * * * *